United States Patent
Lutz et al.

(10) Patent No.: US 11,344,493 B2
(45) Date of Patent: May 31, 2022

(54) CLEAVABLE SURFACTANT

(71) Applicant: FIRMENICH SA, Geneva (CH)

(72) Inventors: Eric Lutz, Pessac (FR); Nicolas Giuseppone, Hangenbieten (FR); Andreas Herrmann, Geneva (CH); Vera Tchakalova, Geneva (CH); Daniel Benczedi, Geneva (CH)

(73) Assignee: FIRMENICH SA, Satigny (CH)

(*) Notice: Subject to any disclaimer, the term of this patent is extended or adjusted under 35 U.S.C. 154(b) by 0 days.

(21) Appl. No.: 16/342,523

(22) PCT Filed: Jan. 22, 2018

(86) PCT No.: PCT/EP2018/051474
§ 371 (c)(1),
(2) Date: Apr. 16, 2019

(87) PCT Pub. No.: WO2018/134410
PCT Pub. Date: Jul. 26, 2018

(65) Prior Publication Data
US 2019/0247294 A1    Aug. 15, 2019

(30) Foreign Application Priority Data

Jan. 23, 2017  (EP) .................................. 17305069

(51) Int. Cl.
| | | |
|---|---|---|
| *A61K 8/86* | (2006.01) | |
| *A23L 27/20* | (2016.01) | |
| *A61K 8/35* | (2006.01) | |
| *A61Q 13/00* | (2006.01) | |
| *C07C 251/12* | (2006.01) | |
| *C08G 65/331* | (2006.01) | |
| *A61K 8/84* | (2006.01) | |
| *C11D 1/00* | (2006.01) | |
| *C11D 3/50* | (2006.01) | |

(Continued)

(52) U.S. Cl.
CPC ............ *A61K 8/86* (2013.01); *A23L 27/202* (2016.08); *A61K 8/35* (2013.01); *A61K 8/84* (2013.01); *A61Q 13/00* (2013.01); *C07C 251/12* (2013.01); *C07C 251/24* (2013.01); *C08G 65/331* (2013.01); *C11D 1/008* (2013.01); *C11D 1/72* (2013.01); *C11D 3/50* (2013.01); *C11D 3/507* (2013.01); *A23V 2002/00* (2013.01); *A23V 2200/15* (2013.01); *A61K 2800/49* (2013.01)

(58) Field of Classification Search
CPC ... A61K 8/86; A61K 8/84; A61K 8/35; A61K 2800/49; A61Q 13/00; C11D 3/507; C11D 1/008; C11D 3/50; C11D 1/72; A23L 27/202; C08G 65/331; A23V 2200/15; A23V 2002/00; C07C 251/12; C07C 251/24
See application file for complete search history.

(56) References Cited

U.S. PATENT DOCUMENTS

| | | | |
|---|---|---|---|
| 4,396,670 A | 8/1983 | Sinclair | |
| 2003/0073607 A1* | 4/2003 | Smets ................... | C11D 3/507 512/27 |

(Continued)

FOREIGN PATENT DOCUMENTS

| | | |
|---|---|---|
| EP | 0 971 025 A1 | 1/2000 |
| WO | 2000002986 A2 | 1/2000 |
| WO | 01/41915 A1 | 6/2001 |

OTHER PUBLICATIONS

Lutz, Eric. "Dynamic covalent surfactants for the controlled release of bioactive volatiles." Other. Universite de Strasbourg, 2014. English. pp. 1-254. (Year: 2014).*

(Continued)

*Primary Examiner* — Doan T Phan
(74) *Attorney, Agent, or Firm* — Armstrong Teasdale LLP

(57) ABSTRACT

Cleavable surfactants of formula (I)

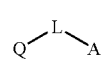

(I)

having a total hydrophilic-lipophilic balance (HLB) of between 3 and 18 and wherein A is a group capable of releasing a flavor or fragrance aldehyde of formula $(R^1)$ CHO or a flavor or fragrance ketone of formula $(R^1)(R^2)$CO and is of formula

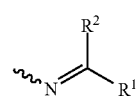

(II)

wherein the wavy line indicates the location of the bond between L and A; $R^1$ and $R^2$ represent a hydrogen atom or a saturated or unsaturated $C_1$-$C_{18}$ hydrocarbon group, provided that at least one of the $R^1$ or $R^2$ groups has 6 consecutive carbon atoms and that both $R^1$ and $R^2$ taken together comprise a maximum of 18 carbon atoms; and L is a linear, branched or cyclic, saturated or unsaturated $C_3$ to $C_{40}$ hydrocarbon group. These surfactants solubilize and/or stabilize flavor and fragrance aldehydes and ketones in an aqueous environment and at the same time to control their release by hydrolysis.

18 Claims, 6 Drawing Sheets

(51) Int. Cl.
  *C07C 251/24* (2006.01)
  *C11D 1/72* (2006.01)

(56) References Cited

U.S. PATENT DOCUMENTS

| | | | |
|---|---|---|---|
| 2008/0227676 A1* | 9/2008 | Bettiol | C11D 3/37 510/106 |
| 2009/0306196 A1 | 12/2009 | Lehn et al. | |
| 2012/0010202 A1* | 1/2012 | Taden | C07D 265/16 514/230.5 |

OTHER PUBLICATIONS

Van et al. "Use of renewable resource vanillin for the preparation of benzoxazine resin and reactive monomeric surfactant containing oxazine ring." Polymer, 55(6): 1443-1451, dated Mar. 2014. (Year: 2014).*

International Search Report and Written Opinion, Appl. No. PCT/EP2018/051474, dated Apr. 30, 2018.

Bonatz et al., "Amino resin microcapsules. III. Release properties," Acta Polymerica, 40(11): 683-690, dated Nov. 1989.

Bône et al., "Microencapsulated Fragrances in Melamine Formaldehyde Resins," Chimia, 65(3): 177-181, dated Mar. 2011.

Davis, "Factors determining emulsion type: Hydrophile-lipophile balance and beyond," Colloids and Surfaces A: Physiochemical and Engineering Aspects, 91: 9-24, Nov. 3, 1994.

Dietrich et al., "Amino resin microcapsules. I. Literature and patent review," Acta Polymerica, 40(4): 243-251, dated Apr. 1989.

Dietrich et al., "Amino resins microcapsules. II. Preparation and morphology," Acta Polymerica, 40(5): 325-331, dated May 1989.

Dietrich et al., "Amino resin microcapsules. IV. Surface tension of the resins and mechanism of capsule formation," Acta Polymerica, 41(2): 91-95, dated Feb. 1990.

Falco et al., "Über die cyclisierung Schiffscher Basen zu methyl-, phenyl- und benzyl-tetrahydroisochinolinen," Tetrahedron, 28(24): 5999-6005 (1972).

Guo et al., "Calculation of hydrophile-lipophile balance for polyethoxylated surfactants by group contribution method," Journal of Colloid and Interface Science, 298(1): 441-450, dated Jun. 2006.

Kametani et al., "The structure of sendaverine and its total synthesis," Tetrahedron Letters, 6(48): 4317-4326 (1965).

Lee et al., "Microencapsulation of fragrant oil via in situ polymerization: effects of pH and melamine-formaldehyde molar ratio," J. Microencapsulation, 19(5): 559-569, dated Sep. 2002.

Nguyen et al., "Dynamic Combinatorial Evolution within Self-Replicating Supramolecular Assemblies," Angew. Chem. Int. Ed., 48(6): 1093-1096 (2009).

Pasquali et al., "Some considerations about the hydrophilic-lipophilic balance system," International Journal of Pharmaceutics, 356(1-2): 44-51, dated May 2008.

Van et al., "Use of renewable resource vanillin for the preparation of benzoxazine resin and reactive monomeric surfactant containing oxazine ring," Polymer, 55(6): 1443-1451, dated Mar. 2014.

Yaozhong et al., "Solid-liquid phase transfer catalytic synthesis of α- amino acid via alkylation and nucleophilic addition of benzaldehyde imines," Tetrahedron, 44(17): 5343-5353 (1988).

"The HLB System, a time-saving guide to emulsifier selection," retrieved from the Internet: http://www.firp.ula.ve/archivos/historicos/76_Book_HLB_ICI.pdf; retrieved on Oct. 16, 2015.

* cited by examiner

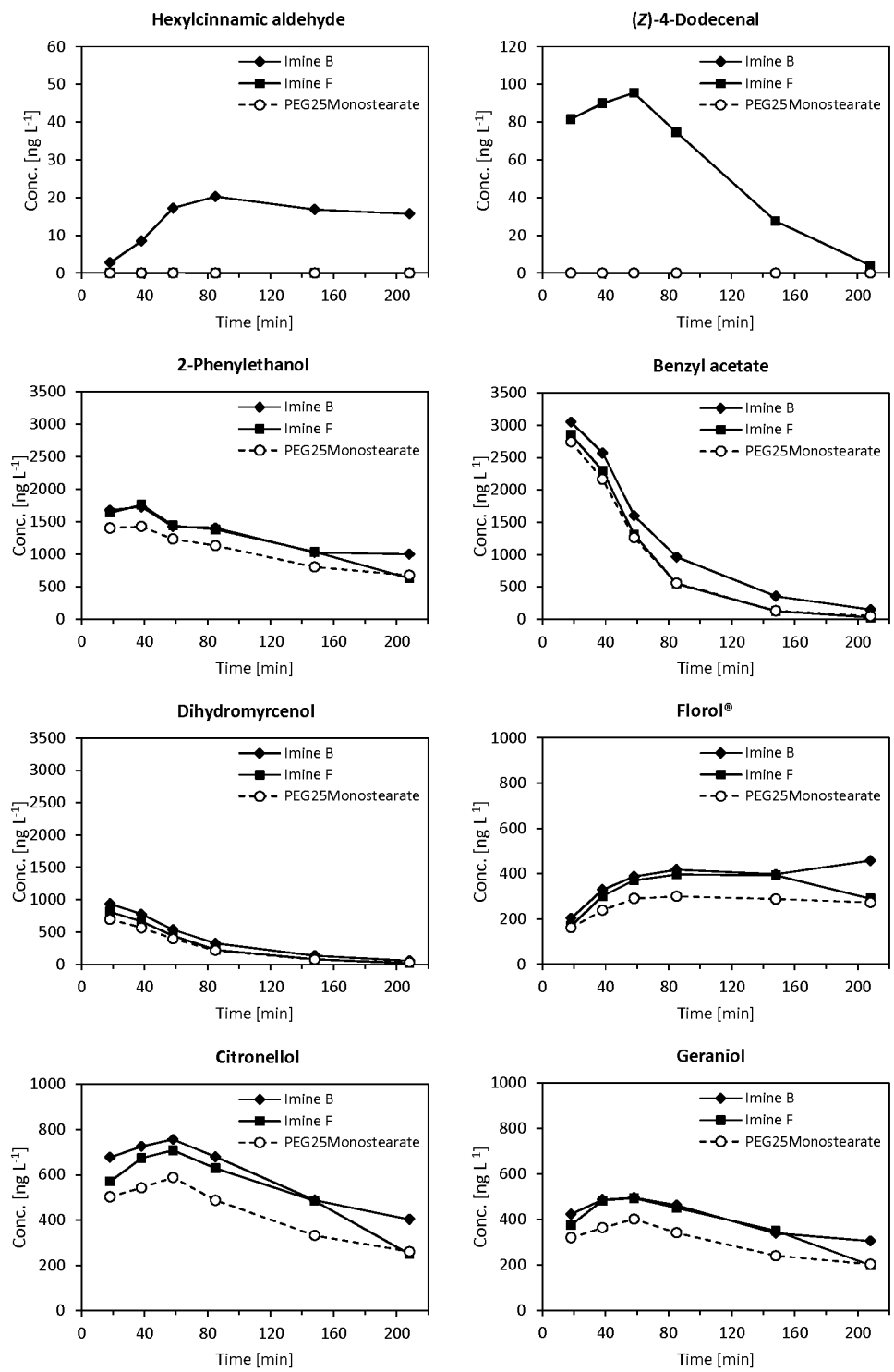
Figure 4 (Part 1)

Figure 4 (Part 2)
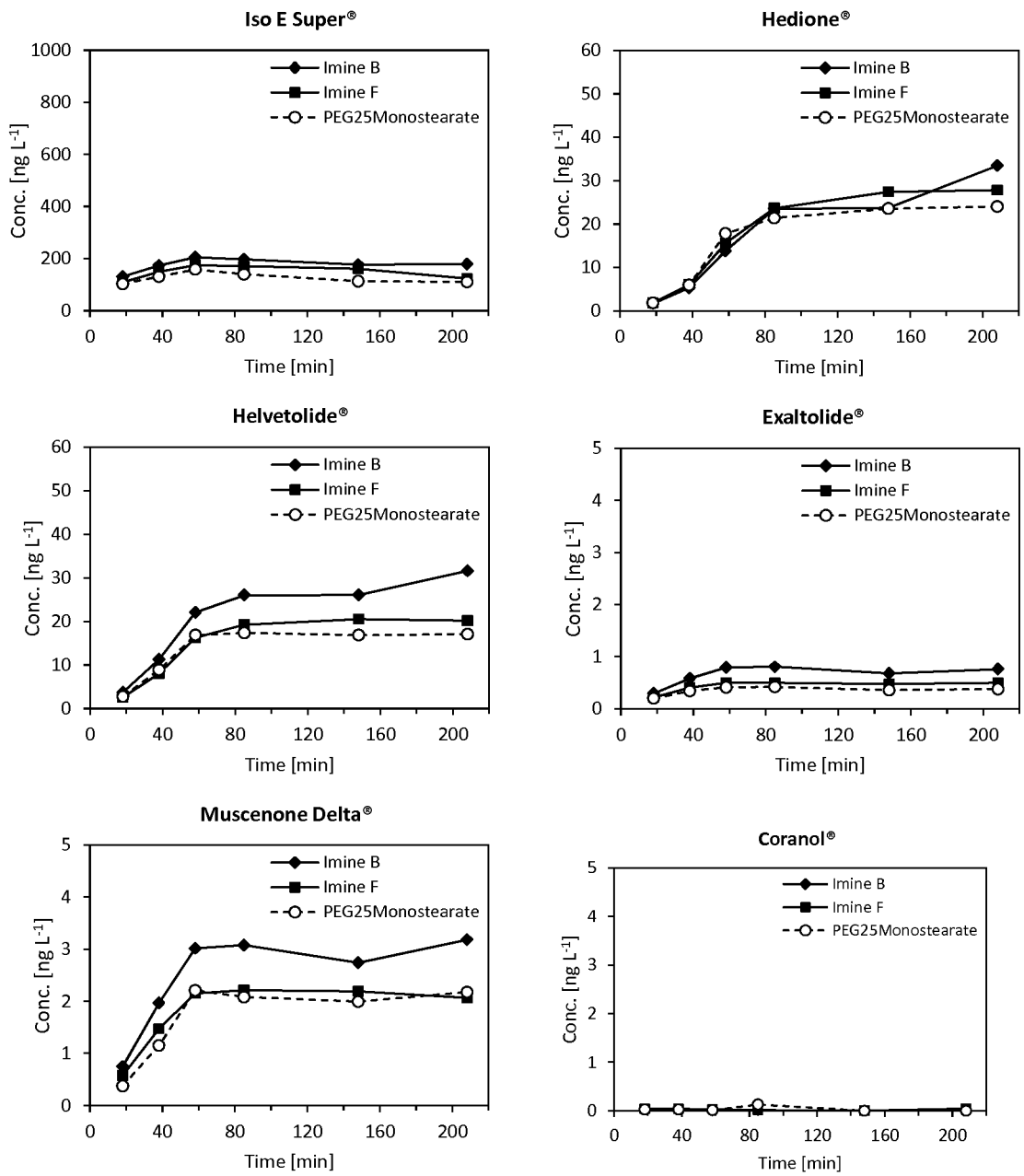

Figure 5 (Part 1)
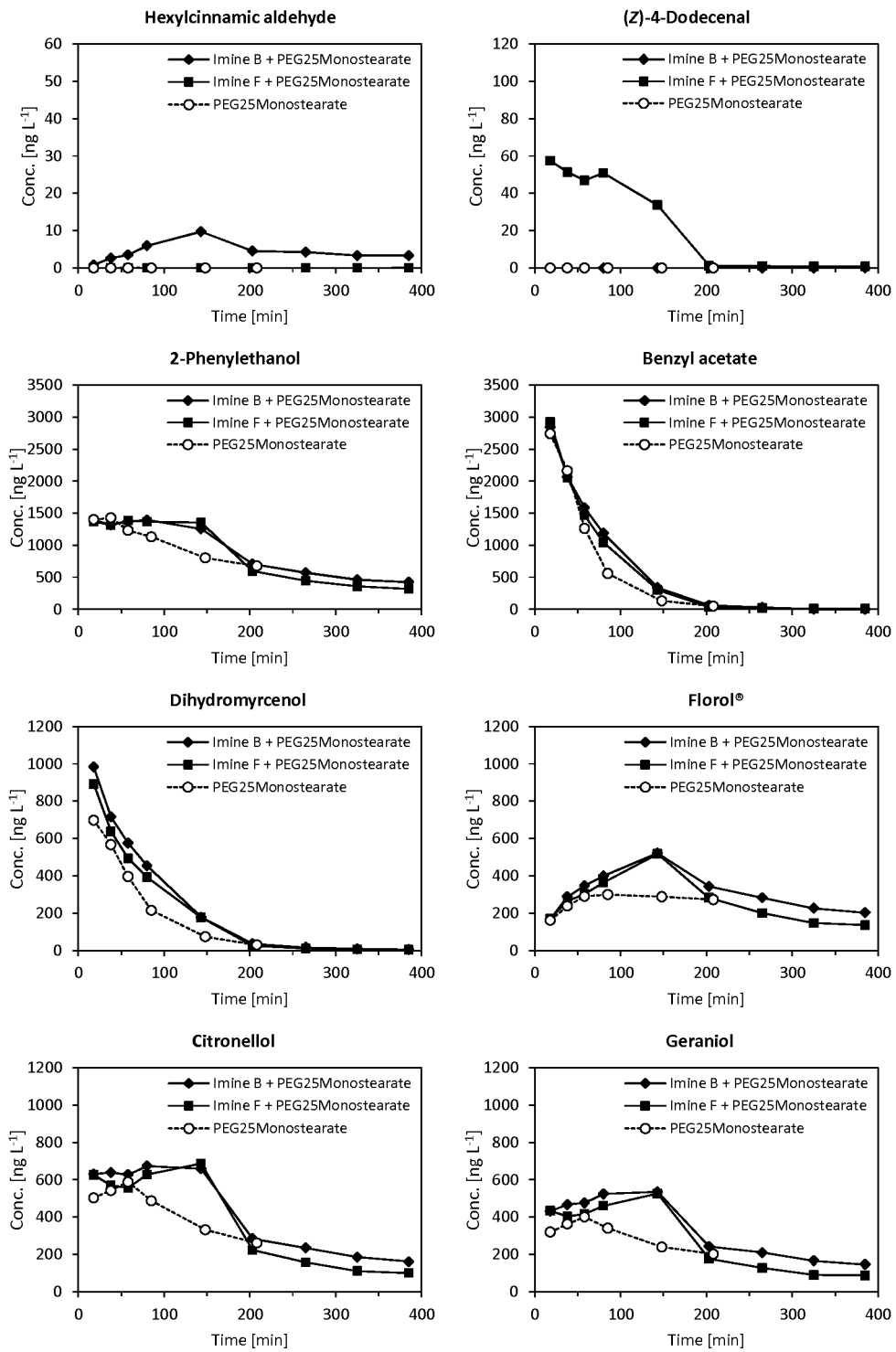

Figure 5 (Part 2)
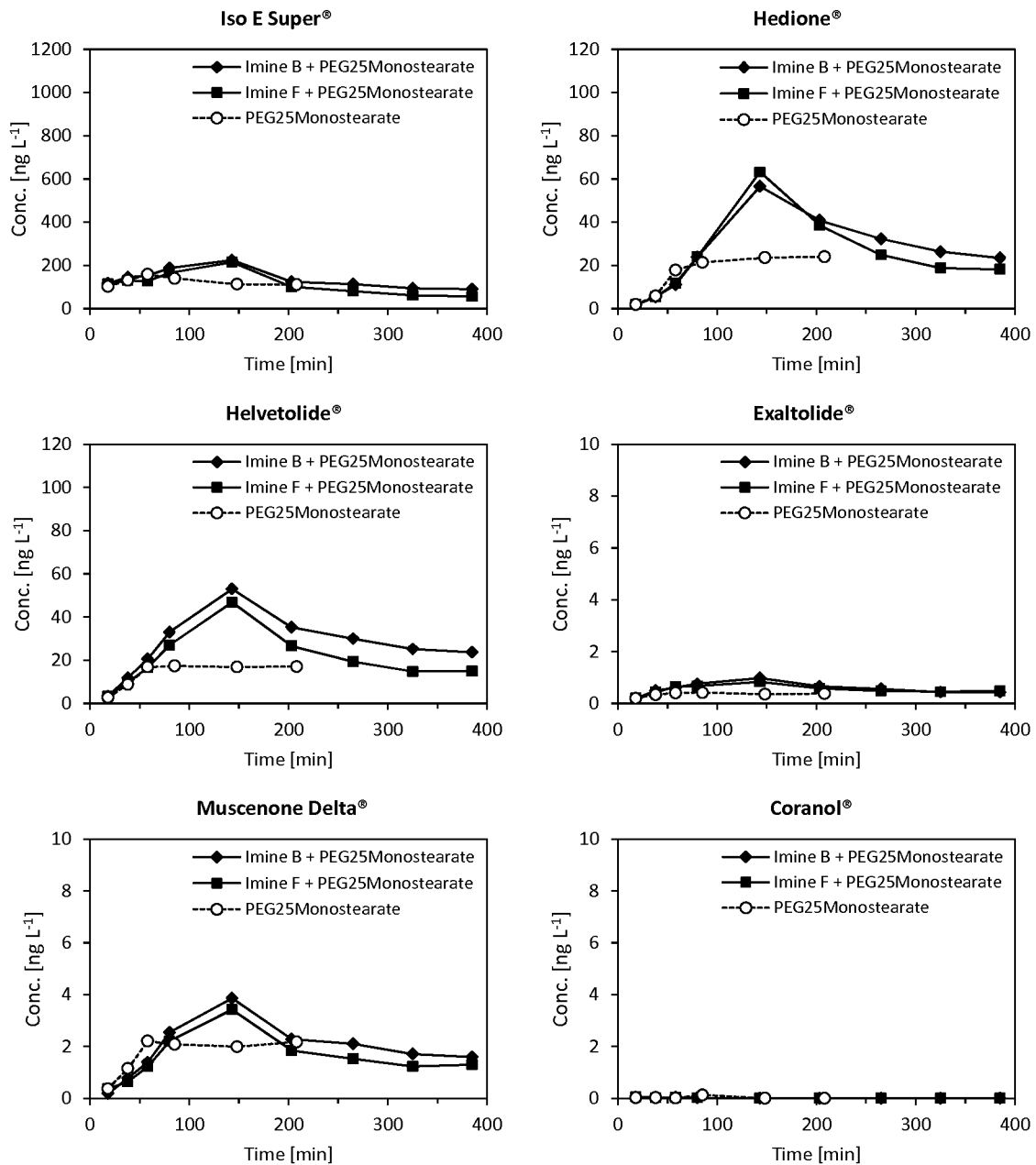

CLEAVABLE SURFACTANT

This application is a 371 filing of International Patent Application PCT/EP2018/051474 filed Jan. 22, 2018, which claims the benefit of European application no. 17305069.1 filed Jan. 23, 2017.

TECHNICAL FIELD

The present invention relates to the field of perfumery and flavor. More particularly, it concerns cleavable surfactants allowing solubilizing and/or stabilizing flavor and fragrance aldehydes and ketones in an aqueous environment and at the same time to control their release by hydrolysis.

BACKGROUND

Many flavor and fragrance aldehydes and ketones are hardly soluble in aqueous consumer product formulations and/or slowly degrade over time, thus reducing their impact in delivering a long-lasting flavor or fragrance perception in application. One typical example is citral which is present in all citrus flavors. It degrades rapidly in contact with water, especially under acidic conditions such as in most beverages. Citral degradation changes the taste and the olfactive profile of citrus flavors and presents one of the biggest issues in citrus applications.

These problems are often tackled through the use of delivery systems, e.g. capsules containing a perfume or a flavor, to release them in a controlled manner. However many types of microcapsules are known to lose parts of the fragrance or flavor during storage, via diffusion through their shells or walls, or as a result of the nature of the consumer product into which they are incorporated and which contains surface active ingredients capable of causing leakage of the perfume or flavor.

As an alternative to encapsulation systems, a variety of precursor compounds which release active material by a chemical reaction during or after application (using $O_2$, light, enzymes, water (pH) or temperature as the release trigger) have been described. One example of precursor compounds are imine-based compounds as reported, for example, in EP0971025, also known as Schiff bases. However, the imine bond is readily hydrolyzed in water and therefore the corresponding precursor is usually not stable in an aqueous environment. Therefore, the precursor compounds comprising an imine bond often decompose in the application during storage, thus liberating an insoluble and unstable compound.

So there is still a need to develop a delivery system allowing solubilizing, stabilizing and releasing in a control manner aldehydes or ketones.

The present invention provides a solution to the above mentioned problem by using cleavable imine surfactants according to the present invention, which are able to temporarily solubilize and/or stabilize flavor and fragrance aldehydes and ketones in an aqueous environment, and release them into the environment by cleavage of the imine bond.

SUMMARY OF THE INVENTION

The invention relates to the use of a cleavable imine surfactant allowing stabilizing and solubilizing flavoring or perfuming aldehydes and ketones while controlling the slow release of said aldehyde or ketone. Unexpectedly, it has been found that the present invention's surfactant organizes in an aqueous medium into a micelle or vesicle and thus protects the imine from hydrolysis. At the same time the invention's surfactant solubilizes organic compounds such as flavors or fragrances in an aqueous environment. The present invention's surfactant thus limits the degradation of the flavor or perfume during storage of the consumer product.

A first object of the present invention is therefore a compound of formula

(I)

having a total hydrophilic-lipophilic balance comprised between 3 and 18 and wherein A is a group capable of releasing a flavor or fragrance aldehyde of formula $(R^1)$CHO or a flavor or fragrance ketone of formula $(R^1)(R^2)$CO and is of formula

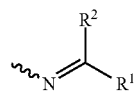

(II)

wherein the wavy line indicates the location of the bond between L and A; $R^1$ and $R^2$ represent independently from each other a hydrogen atom or a linear saturated or unsaturated $C_1$-$C_{18}$ hydrocarbon group, optionally substituted with one to three oxygen atoms in the form of a hydroxyl, carbonyl, ether or ester group, or a branched or cyclic, saturated or unsaturated $C_3$-$C_{18}$ hydrocarbon group, optionally substituted with one to three oxygen atoms in the form of a hydroxyl, carbonyl, ether or ester group or $R^1$ and $R^2$, when taken together, represent a $C_{4-18}$ linear, branched or cyclic alkanediyl group, optionally substituted with one to three oxygen atoms in the form of a hydroxyl, carbonyl, ether or ester group, provided that at least one of the $R^1$ or $R^2$ groups has 6 consecutive carbon atoms and that both $R^1$ and $R^2$ taken together comprise a maximum of 18 carbon atoms;

L is a linear, branched or cyclic, saturated or unsaturated $C_3$ to $C_{40}$ hydrocarbon group, optionally substituted with one to twelve oxygen atoms in the form of an ether or ester group; and Q is a branched, linear, cyclic, saturated or unsaturated $C_3$ to $C_{100}$ hydrocarbon group different than L, optionally substituted with 1 to 50 oxygen atoms, or with 1 to 50 nitrogen atoms or with 1 to 10 sulphur atoms.

A second object of the invention is the use of a compound of formula (I) as defined above as surfactant.

A third object of the present invention is a solubilizing system comprising water, perfuming or flavoring oil and at least one surfactant of formula (I) as defined above.

Another object of the present invention is the use of a compound of formula (I) or the solubilizing system as defined above as a delivery system to release active volatile aldehydes or ketones.

Another object of the present invention is a perfuming or flavoring composition comprising:
i) as perfuming or flavoring ingredient, at least one of the invention's compounds and/or solubilizing systems as defined above;
ii) at least one ingredient selected from the group consisting of a perfumery or flavor carrier, a perfuming or flavoring co-ingredient and mixtures thereof; and iii) optionally at least one perfumery or flavor adjuvant.

Another object of the present invention is a perfuming or flavoring consumer product comprising at least one compound of formula (I) and/or a solubilizing system, as defined above.

Another object of the present invention is a method to release active volatile aldehydes or ketones by applying to a composition, an article or a surface at least one compound of formula (I) as defined above and/or a solubilizing system as defined above.

A last object of the present invention is a method to solubilize and/or stabilize hydrophobic molecules in an aqueous environment by adding to said aqueous an effective amount of at least one compound of formula (I) as defined above.

BRIEF DESCRIPTION OF THE DRAWINGS

FIG. 4: Dynamic headspace concentrations measured for the evaporation of the ingredients of a model perfume solubilized in water with an imine according to formula (I) as compared to a commercial surfactant ($PEG_{25}$Monostearate).

FIG. 5: Dynamic headspace concentrations measured for the evaporation of the ingredients of a model perfume solubilized in water with a mixture of an imine according to formula (I) and a commercial surfactant ($PEG_{25}$Monostearate) in a 1:1 molar ratio as compared to a single commercial surfactant ($PEG_{25}$Monostearate).

DESCRIPTION OF THE INVENTION

Figure 1:
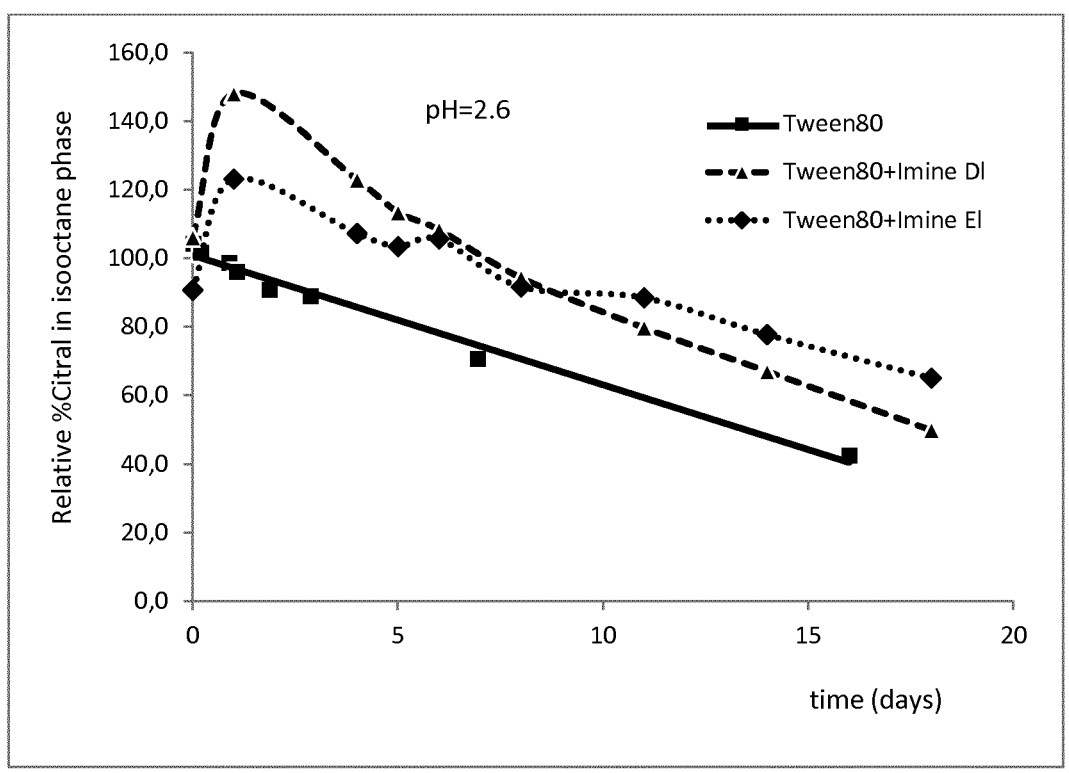
FIG. 1: Kinetics of citral degradation determined for the different formulations comprising free citral and/or a surfactant of the present invention as defined in Table 10.

We have now surprisingly discovered that amphiphilic imine surfactants according to formula (I) composed of a hydrophilic part Q, an intermediate section L (linker) and a hydrophobic part A derived from a flavor or fragrance aldehyde or ketone and having a total hydrophilic-lipophilic balance (HLB) comprised between 3 and 18 are able to solubilize flavor or fragrance oils in an aqueous environment and/or to stabilize flavor and fragrance compounds against premature degradation. Actually, the imines according to formula (I) are able to form organized aggregates in a water-based formulation protecting the imine against hydrolysis. Modification of the external conditions triggers the controlled release of aldehyde or ketone into the environment by hydrolysis.

The first object of the present invention is a compound of formula

(I)

having a total hydrophilic-lipophilic balance (HLB) comprised between 3 and 18 and wherein
A is a group capable of releasing a flavor or fragrance aldehyde of formula $(R^1)CHO$ or a flavor or fragrance ketone of formula $(R^1)(R^2)CO$ and is of formula

(II)

wherein the wavy line indicates the location of the bond between L and A; $R^1$ and $R^2$ represent independently from each other a hydrogen atom or a linear saturated or unsaturated $C_1$-$C_{18}$ hydrocarbon group, optionally substituted with one to three oxygen atoms in the form of a hydroxyl, carbonyl, ether or ester group, or a branched or cyclic, saturated or unsaturated $C_3$-$C_{18}$ hydrocarbon group, optionally substituted with one to three oxygen atoms in the form of a hydroxyl, carbonyl, ether or ester group or $R^1$ and $R^2$, when taken together, represent a $C_{4-18}$ linear, branched or cyclic alkanediyl group, optionally substituted with one to three oxygen atoms in the form of a hydroxyl, carbonyl, ether or ester group, provided that at least one of the $R^1$ or $R^2$ groups has 6 consecutive carbon atoms and that both $R^1$ and $R^2$ taken together comprise a maximum of 18 carbon atoms;
L is a linear, branched or cyclic, saturated or unsaturated $C_3$ to $C_{40}$ hydrocarbon group, optionally substituted with one to twelve oxygen atoms in the form of an ether or ester group; and
Q is a branched, linear, cyclic, saturated or unsaturated $C_3$ to $C_{100}$ hydrocarbon group different than L, optionally substituted with 1 to 50 oxygen atoms, or with 1 to 50 nitrogen atoms or with 1 to 10 sulphur atoms.

In other words, the first object of the present invention is a surfactant of formula

(I)

having a total hydrophilic-lipophilic balance (HLB) comprised between 3 and 18 being calculated using the effective chain length model and wherein
A is a group capable of releasing a flavor or fragrance aldehyde of formula $(R^1)CHO$ or a flavor or fragrance ketone of formula $(R^1)(R^2)CO$ and is of formula

(II)

wherein the wavy line indicates the location of the bond between L and A; R and R represent independently from each other a hydrogen atom or a linear saturated or unsaturated $C_1$-$C_{18}$ hydrocarbon group, optionally substituted with one to three oxygen atoms in the form of a hydroxyl, carbonyl, ether or ester group, or a branched or cyclic, saturated or unsaturated $C_3$-$C_{18}$ hydrocarbon group, optionally substituted with one to three oxygen atoms in the form of a hydroxyl, carbonyl, ether or ester group or $R^1$ and $R^2$, when taken together, represent a $C_{4-18}$ linear, branched or cyclic alkanediyl group, optionally substituted with one to three oxygen atoms in the form of a hydroxyl, carbonyl, ether or ester group, provided that at least one of the $R^1$ or $R^2$ groups has 6 consecutive carbon atoms and that both $R^1$ and $R^2$ taken together comprise a maximum of 18 carbon atoms;

L is a linear, branched or cyclic, saturated or unsaturated $C_3$ to $C_{40}$ hydrocarbon group, optionally substituted with one to twelve oxygen atoms in the form of an ether or ester group; and Q is a branched, linear, cyclic, saturated or unsaturated $C_3$ to $C_{100}$ hydrocarbon group different than L, optionally substituted with 1 to 50 oxygen atoms, or with 1 to 50 nitrogen atoms or with 1 to 10 sulphur atoms.

The compound of formula (I) is composed of a hydrophobic part A [N=C($R^1$)($R^2$)], a linker L, and a hydrophilic part Q.

By the expression "6 consecutive carbon atoms" or similar, it is meant the normal meaning in the art; i.e. $R^1$ or $R^2$ or $R^1$ and $R^2$ when taken together comprise at least 6 carbon atoms linked together one after the other. Said 6 consecutive carbon atoms can be part of an aliphatic hydrocarbon, can be a cycle, or can be a part of a cycle. Said 6 consecutive carbon atoms can be substituted by alkyl or alkenyl groups.

The term "total hydrophilic-lipophilic balance" (HLB) has the normal meaning in the art; i.e. the HLB characterizes the solubility of a surfactant and is the balance between the hydrophilic part and the hydrophobic part of the compound of formula (I). The HLB characterizes the ability of a compound to form organized aggregates and the aggregate geometry; i.e. micelle, vesicle, lamellae. The HLB of compounds of formula (I) can be calculated/obtained by using the so-called effective chain length (ECL) model (modified Davis's method) based on group properties as reported by X. Guo, Z. Rong and X. Ying, *Journal of Colloid and Interface Science* 2006, vol. 298, pages 441-450. To estimate the role of each part of the compounds according to formula (I), the HLB is considered as a sum of 3 components: HLB (Q) of the hydrophilic part, HLB (L) of the linker and HLB (A) of the hydrophobic part. The total HLB of a compound according to formula (I) is calculated according to Equation 1

$$HLB = 7 + HLB(Q) + HLB(L) + HLB(A) \quad \text{Equation 1}$$

wherein $HLB(Q) = GN_{CH3} + GN_{EO} * N_{EO}^{eff} + \Sigma G_i N_i$ (other hydrophilic groups)

$HLB(L) = GN_{PO} * N_{PO}^{eff} + \Sigma G_j N_j$ (other lipophilic groups)

$HLB(A) = GN_{CH2} * N_{CH2}^{eff} + \Sigma G_j N_j$ (other lipophilic groups)

wherein $GN_{CH2}$ is the group number of a $CH_2$ group, $GN_{CH3}$ is the group number of a $CH_3$ group, $GN_{EO}$ is the group number of an ethylene oxide (EO) group, $GN_{i,j}$ is the group number of a hydrophilic or lipophilic group respectively and $GN_{PO}$ is the group number of a propylene oxide (PO) group, and wherein $N_{i,j}$ is the number of hydrophilic or lipophilic group respectively; $N_{CH2}^{eff}$ is the $CH_2$ effective chain length defined as $$N_{CH2}^{eff} = 0.965 * N_{CH2} - 0.178$$

with $N_{CH2}$ being the number of $CH_2$ groups; $N_{EO}^{eff}$ is the EO effective chain length defined as $$N_{EO}^{eff} = 13.45 * \ln(N_{EO}) - 0.16 * N_{EO} + 1.26 \text{ for } N_{EO} \leq 50$$

with $N_{EO}$ being the number of EO groups; $N_{PO}^{eff}$ is the PO effective chain length defined as $$N_{PO}^{eff} = 2.057 * N_{PO} + 9.06$$

and with $N_{PO}$ being the number of PO groups. Values of the group numbers following ECL method have been used as reported in the literature by X. Guo, Z. Rong and X. Ying, *Journal of Colloid and Interface Science* 2006, vol. 298, pages 441-450 and as reported in Table 1. The imine group has been considered as tertiary imine and the group number 2.4 was used for imine group.

TABLE 1

The group number obtained by ECL method

| Group | ECL method |
|---|---|
| —SO4Na | 38.4 |
| —COOK | 20.8 |
| —COONa | 18.8 |
| —SO3Na | 10.7 |
| —N (tertiary amine) | 2.4 |
| Ester (free) | 2.316 |
| —COOH | 1.852 |
| —OH (free) | 2.255 |
| —CH2OH | 0.724 |
| —CH2CH2OH | 0.479 |
| —CH2CH2CH2OH | 0.382 |
| —O— | 1.30 |
| —CH2CH2O— | 0.33 |
| —CH2CH2OOC— | 3.557 |
| —OH (sorbitan ring) | 5.148 |
| Ester (sorbitan ring) | 11.062 |
| —CH— | −0.48 |
| —CH2— | −0.48 |
| —CH3 | −0.48 |
| =CH— | −0.48 |
| —CF2— | — |
| —CF3 | — |
| Phenyl | −1.60 |
| —CH2CH2CH2O— | −0.15 |
| —CH(CH3)CH2O— | −0.15 |
| —CH2CH(CH3)O— | −0.15 |
| Sorbitan ring | −20.57 |

The HLB values characterizing the surface activity of molecules should lie in the range from 3 to 18. Below and above these limits, the molecules are solubilized preferentially in the polar or non-polar phase and thus they will not form organized aggregates.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies. In all the embodiments of the invention, when it is mentioned that the hydrocarbon group may be optionally substituted with heteroatom such as oxygen atom, nitrogen atom or sulphur atoms, it is meant that the hydrogen atom of the hydrocarbon group may be substituted by a heteroatom and also a carbon atom may be substituted by a heteroatom; i.e. the hydrocarbon group being a polyol or a polyamine.

A, L and Q in formula (I) are selected in a way, that the part A-L is more hydrophobic than Q, and that the compound of formula (I) is able to form an organized aggregate in an aqueous environment.

According to any one of the above embodiments of the invention, the total hydrophilic-lipophilic balance (HLB) may be comprised between 3 and 18, preferably between 4 and 18. Even more preferably, the total hydrophilic-lipophilic balance (HLB) may be comprised between 10 and 18, preferably, between 10 and 16, even more preferably, between 10 and 15. The total hydrophilic-lipophilic balance (HLB) may be about 11, about 12, about 13, about 14.

According to a particular embodiment of the invention, the total hydrophilic-lipophilic balance (HLB) may be comprised between 3 and 10.

According to any one of the above embodiments of the invention, the compound of the invention is of formula

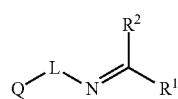

(III)

wherein Q, L, $R^1$ and $R^2$ have the same meaning as above.

According to any one of the above embodiments of the invention, L may represent a linear, branched or cyclic, saturated or unsaturated $C_6$ to $C_{30}$ hydrocarbon group, optionally substituted with one to twelve oxygen atoms in the form of an ether group. Preferably, L may represent a $C_6$ to $C_{30}$ polyalkyl glycol having from 3 to 10 repeating units or a $C_7$ to $C_{14}$ alkyl phenoxy group. Preferably, L may represent a $OC_6H_4CR^3{}_2CR^3{}_2$ group or a $(OCH_2CHR^3)_q$ group wherein $R^3$ represents a hydrogen atom or a methyl group and q is an integer varying between 3 and 10. Preferably, L may represent a $OC_6H_4CH_2CH_2$ group or a $(OCH_2CH(CH_3))_q$ group wherein q is an integer varying between 3 and 10, even more preferably q is 3 or 10.

According to any one of the above embodiments of the invention, Q may represent a branched, linear, cyclic, saturated or unsaturated $C_3$ to $C_{100}$ hydrocarbon group different than L, optionally substituted with 1 to 50 oxygen atoms, or with 1 to 50 nitrogen atoms or with 1 to 10 sulphur atoms. Preferably, Q may represent a branched, linear, cyclic, saturated or unsaturated $C_3$ to $C_{100}$ hydrocarbon group different than L, optionally substituted with 1 to 50 oxygen atoms or with 1 to 10 sulphur atoms. Q may represent a polyimine, a polysaccharide, a poly(ethylene oxide), a poly (propylene oxide) or a polypeptide. Preferably, Q may represent a polysaccharide, a poly(ethylene oxide), a poly (propylene oxide) or a polypeptide. Even more preferably, Q may represent a poly(ethylene oxide), a poly(propylene oxide) or a polypeptide. Even more preferably, Q may represent a $T(OC_2H_4)_m$ group or $T(OC_3H_6)_m$ group wherein m being an integer varying between 7 and 40 and T is a terminating group being H atom or methyl group. Preferably, Q may represent a $CH_3(OC_2H_4)_m$ group wherein m is an integer varying between 11 and 30. Most preferably, m is 11, 19 or 30.

According to any one of the above embodiments of the invention, the Q-L part of the compound of formula (I) may be a block copolymer of polyethylene glycol and polypropylene glycol wherein the molar ratio between polypropylene glycol and polyethylene glycol is in the range comprised between 1:3 to 5:1. Said block copolymers are usually not monodisperse and are mixtures of polymers with different chain lengths varying around an average structure and thus resulting in a certain molecular weight distribution. For the calculation of the HLB and the designation of compound names reference is always made to the average structures of the polymers.

According to any one of the above embodiments, the compound of formula (I) is capable of releasing a compound of formula $$Q\text{-}L\text{-}NH_2 \qquad\qquad (IV)$$

and a flavor or fragrance aldehyde of formula $(R^1)CHO$ or a flavor or fragrance ketone of formula $(R^1)(R^2)CO$; wherein Q, L, $R^1$ and $R^2$ have the same meaning as above. The release is triggered in an aqueous medium by modifying the concentration and/or the pH.

According to any one of the above embodiments of the invention, the compound of formula (IV) Q-L-$NH_2$ is a polyetheramine also known as polyether monoamine such as those sold under the trademark Jeffamine® (trademark from Huntsman and commercially available from Huntsman). Preferably, the compound of formula (IV) is a Jeffamine® M. Even more preferably, the Q-L-$NH_2$ may be a polymer selected from the group consisting of Jeffamine® M-2070 and Jeffamine® M-1000.

According to any one of the above embodiments, $R^1$ and $R^2$ may represent independently from each other a hydrogen atom or a linear saturated or unsaturated $C_1$-$C_{18}$ hydrocarbon group, optionally substituted with one to three oxygen atoms in the form of a hydroxyl, carbonyl, ether or ester group, or a branched or cyclic, saturated or unsaturated $C_3$-$C_{18}$ hydrocarbon group, optionally substituted with one to three oxygen atoms in the form of a hydroxyl, carbonyl, ether or ester group or $R^1$ and $R^2$, when taken together, represent a $C_{4-18}$ linear, branched or cyclic alkanediyl group, optionally substituted with one to three oxygen atoms in the form of a hydroxyl, carbonyl, ether or ester group, provided that at least one of the $R^1$ or $R^2$ groups has 8 consecutive carbon atoms.

In an even more preferred embodiment, said active aldehydes of formula $R^1CHO$ are selected from the group consisting of 1,3-benzodioxol-5-carboxaldehyde (heliotropine), 3-(1,3-benzodioxol-5-yl)-2-methylpropanal, 2,4-decadienal, 2-decenal, 4-decenal, 8-decenal, 9-decenal, 3-(6, 6-dimethyl-bicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 5,9-dimethyl-4,8-decadienal, 5,9-dimethyldec-8-enal, 2,6-dimethyl-5-heptenal (melonal), 3,7-dimethyl-2,6-octadienal (citral), 3,7-dimethyloctanal, 3,7-dimethyl-6-octenal (citronellal), 2-dodecenal, 3-dodecenal, 4-dodecenal, 3-ethoxy-4-hydroxybenzaldehyde (ethyl vanillin), 4-ethyl benzaldehyde, 3-(2 and 4-ethylphenyl)-2,2-dimethylpropanal, 2,4-heptadienal, 4-heptenal, 2-hexenal, 3-hexenal, 2-hexyl-3-phenyl-2-propenal (hexylcinnamic aldehyde), 2-hydroxybenzaldehyde, 7-hydroxy-3,7-dimethyloctanal (hydroxycitronellal), 4-hydroxy-3-methoxybenzaldehyde (vanillin), 4- and 3-(4- hydroxy-4-methylpentyl)-3-cyclohexene-1-carbaldehyde (Lyral®, origin: International Flavors and Fragrances, New York, USA), 4-isopropylbenzaldehyde (cuminaldehyde), 3-(4-isopropylphenyl)-2-methylpropanal, 2-(4-isopropylphenyl)propanal, (4R)-1-p-menthene-9-carbaldehyde (Liminal®, origin: Firmenich SA, Geneva, Switzerland), 4-methoxybenzaldehyde (anisaldehyde), 6-methoxy-2,6-dimethylheptanal (methoxymelonal), 5- and 6-methoxyoctahydro-1H-4,7-methanoindene-1- and 2-carbaldehyde (Scentenal®, origin: Firmenich SA, Geneva, Switzerland), 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 4-(4-methyl-3-pentenyl)-3-cyclohexene-1-carbaldehyde (Empetal, origin: Givaudan-Roure SA., Vernier, Switzerland), (4-methylphenyl)acetaldehyde, 3-methyl-5-phenylpentanal (Phenexal®, origin: Firmenich SA, Geneva, Switzerland), 2-methylundecanal, 2,4-nonadienal, 2,6-nonadienal, nonanal, 2-nonenal, 3-nonenal, 6-nonenal, 8-nonenal, 2-octenal, phenylacetaldehyde, 3-phenylbutanal (Trifernal®, origin: Firmenich SA, Geneva, Switzerland), 2-phenylpropanal (hydratropaldehyde), 3-phenyl-2-propenal (cinnamic aldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1]heptane-3-carbaldehyde (formyl pinane), 2,4, 6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, undecanal, 2-undecenal, 10-undecenal or 9-undecenal and their mixtures such as Intreleven aldehyde (origin: International Flavors & Fragrances, New York, USA) and Aldehyde Supra (origin: Firmenich SA, Geneva, Switzerland.

Respectively, said active ketone of formula $(R^1)(R^2)C(=O)$ is preferably selected from the group consisting of damascenones, damascones, ionones, methyl ionones (such as Iralia® Total, origin: Firmenich SA, Geneva, Switzerland), irones, cyclopentadecanone (Exaltone®, origin: Firmenich SA, Geneva, Switzerland), 3-methyl-4-cyclopentadecen-1-one (origin: Firmenich SA, Geneva, Switzerland), 3-methyl-5-cyclopentadecen-1-one (Delta Muscenone, origin: Firmenich SA, Geneva, Switzerland), 3-methyl-1-cyclopentadecanone (Muscone, origin: Firmenich SA, Geneva, Switzerland), 1-(2-aminophenyl)-1-ethanone, 1-(5,5-dimethyl-1-cyclohexen-1-yl)-4-penten-1-one (Neobutenone®, origin: Firmenich SA, Geneva, Switzerland), 1-(3,3-dimethylcyclohexyl)ethan-1-one, 2,5-dimethyl-2-octen-6-one, 4,7-dimethyl-6-octen-3-one, 1-(2,4-dimethylphenyl)-1-ethanone, 4-(1,1-dimethylpropyl)-1-cyclohexanone (Orivone®, origin: International Flavors & Fragrances, New York, USA), 2,4-di-tert-butyl-1-cyclohexanone, 1-(4-ethylphenyl)-1-ethanone, 2-hexyl-1-cyclopentanone, 4-(4-hydroxy-1-phenyl)-2-butanone (raspberry ketone), 1-(2- and 4-hydroxyphenyl)-1-ethanone, 4-isopropyl-2-cyclohexen-1-one, 1-(4-isopropylphenyl)ethan-1-one, 1(6),8-p-menthadien-2-one (carvone), 4(8)-p-menthen-3-one, 1-(1-p-menthen-2-yl)-1-propanone, menthone, (1R, 4R)-8-mercapto-3-p-menthanone, 1-(4-methoxyphenyl)-1-ethanone, 5-methyl-3-heptanone, 6-methyl-5-hepten-2-one, methyl 3-oxo-2-pentyl-1-cyclopentaneacetate (Hedione®, origin: Firmenich SA, Geneva, Switzerland), 1-(4-methylphenyl)-1-ethanone (4-methylacetophenone), 2-(1-methylpropyl)-1-cyclohexanone, 5-methyl-exo-tricyclo[6.2.1.0 (2,7)]undecan-4-one, 3-methyl-4-(1,2,2-trimethylpropyl)-4-penten-2-one, 2-naphthalenyl-1-ethanone, 1-(octahydro-2,3,8,8-tetramethyl-2-naphthalenyl)-1-ethanone (isomeric mixture, Iso E Super®, origin: International Flavors & Fragrances, New York, USA), 3,4,5,6,6-pentamethyl-3-hepten-2-one, 2-pentyl-1-cyclopentanone (Delphone, origin: Firmenich SA, Geneva, Switzerland), 4-phenyl-2-butanone (benzylacetone), 1-phenyl-1-ethanone (acetophenone), 2- and 4-tert-butyl-1-cyclohexanone, 1-(4-tert-butylphenyl)-1-ethanone), 2,4,4,7-tetramethyl-6-octen-3-one, 1,7,7-trimethyl-bicyclo[2.2.1]heptan-2-one (camphor), 2,6,6-trimethyl-1-cycloheptanone, 2,6,6-trimethyl-2-cyclohexene-1,4-dione, 4-(2,6,6-trimethyl-2-cyclohexen-1-yl)-2-butanone (dihydroionone), 1-(2,4,4-trimethyl-2-cyclohexen-1-yl)-2-buten-1-one, 1-(3,5,6-trimethyl-3-cyclohexen-1-yl)-1-ethanone and 2,2,5-trimethyl-5-pentyl-1-cyclopentanone.

According to any one of the above embodiments of the invention, the compound of the invention is of formula

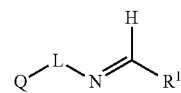

(V)

wherein Q and L have the same meaning as above and $R^1$ is derived from a flavor or fragrance aldehyde of formula $(R^1)CHO$ wherein $R^1$ represents a linear, branched or cyclic, saturated or unsaturated $C_6$-$C_{18}$ hydrocarbon group having at least 6 consecutive carbon atoms, optionally substituted with one to three oxygen atoms in the form of a hydroxyl, carbonyl, ether or ester group. Preferably, $R^1$ is derived from a flavor or fragrance aldehyde selected from the group consisting of benzaldehyde, hexylcinnamic aldehyde, citral and (4Z)-4-dodecenal.

Owing to their particular chemical structure, the invention's compound of formula (I) is capable solubilizing and/or stabilizing flavor and fragrance aldehydes or ketones and of releasing, via a hydrolysis reaction, a compound of formula (IV) and a flavoring or perfuming aldehyde or ketone. In an aqueous medium, the solubilization, stabilization and controlled release of the flavoring or perfuming aldehyde or ketone having 6 consecutive carbon atoms and comprising between 6 and 15 carbon atoms is obtained at a concentration of compound of formula (I) comprised between 0.05% and 95% weight, based on the total weight of the aqueous solution, preferably between 0.1% and 50%, and at a pH comprised between 2 and 11. The person skilled in the art depending of the desired release's rate will be able to select the pH and the concentration.

In all aspects of the above-described invention the invention's compound might be used in the presence of other fragrance delivery systems, in particular in the presence of other aqueous-sensitive fragrance delivery systems, or even in the presence of other delivery systems having a complementary release profile. The invention's compound might also be used in the presence of other surfactants. Suitable surfactants might be selected from sodium dodecyl sulfate (SDS), sodium laureth sulphate (as for example commercialized under the trademark Texapon® NSO IS), hexadecyl-trimethyl-ammonium bromide (cetrimonium bromide), 2,5,8,11,14,17,20,23,26,29,32,35,38,41,44,47,50,53,56,59,62,65,68,71,74-pentacosaoxahexaheptacontan-76-yl stearate ($PEGs_{25}$Monostearate), (polyethylene glycol)$_{9,10}$ 4-(1,1,3,3-tetramethylbutyl)-phenyl ether (as for example commercialized under the trademark Triton® X-100), polyoxyethylene 20 sorbitan monooleate (as for example commercialized under the trademark Tween® 80), sodium $C_{14-17}$ sec-alkyl sulphonate (as for example commercialized under the trademark Hostapur® SAS 60) and ethoxylated $C_{12-16}$ alcohols (as for example commercialized under the trademark Genapol® LA 70).

Another object of the invention is the use of at least one compound of formula (I) as a surfactant, preferably the use of a compound of formula (I) as a surfactant. The compound of formula (I) is an amphiphilic molecule capable, depending on the concentration, to self-organize e.g. as a micelle, liquid-crystalline phases or a vesicle. The use of at least one compound of formula (I) in an aqueous solution allows solubilizing hydrophobic molecules such as perfumery or flavor compounds in an aqueous environment.

As already mentioned, in aqueous medium, cleavable surfactants of the present invention self-organize; e.g. as a micelle, by protecting the labile imine function from hydrolysis. Such organization allows solubilizing, stabilizing and controlling the release of aldehydes and ketones leading to a significantly decreased degradation of aldehydes and ketones during storage of said solubilizing system. So, another object of the invention is a solubilizing system comprising water, perfuming or flavoring oil and at least one surfactant of formula (I) as defined above. Said solubilizing system may be in the form of dispersed perfuming or flavoring ingredient-containing oil droplets stabilized by at least one surfactant of formula (I) in water (e.g. oil-in-water emulsion) or in the form of dispersed water-containing droplets stabilized by at least one surfactant of formula (I) in perfuming or flavoring oil (e.g water-in oil emulsion). Preferably, the solubilizing system comprises water and dispersed perfuming or flavoring ingredient-containing oil droplets stabilized by surfactants of formula (I) as defined above (e.g. oil-in-water emulsion). The different parts A, L and Q of the molecule are selected in a way that the final molecule according to formula (I) is able to form organized aggregates, such as micelles, liquid-crystalline phases or vesicles, in a water containing environment. The presence of a relatively hydrophobic linker L between the hydrophilic part Q and the imine bond is an important parameter to stabilize the imine bond in water and to enable its partial integration into the hydrophobic core of the micelle, and therefore to limit the contact of the imine bond with water.

By the term "solubilizing system", it is meant the normal meaning in the art; i.e. an oil-in-water or water-in-oil emulsion, wherein emulsion includes macroemulsion, nanoemulsion, also called miniemulsion, or microemulsion. Preferably, the invention's solubilizing system is an oil-in-water emulsion. Even more preferably, the invention's solubilizing system is an oil-in-water microemulsion.

The oil droplets have an average diameter comprised between 5 and 1000 nm. The water is present in an amount comprised between 50 wt % and 95 wt %, relative to the total weight of the solubilizing system. The perfuming or flavoring ingredient-containing oil is present in an amount comprised between 0.01 wt % and 15 wt %, relative to the total weight of the solubilizing system. In order to form the aggregates according to the invention, it is important that the one or more surfactants are present in an amount greater than the critical micelle concentration. Critical micelle concentration is abbreviated herein as "CMC". The surfactant of formula (I) is present in an amount comprised between 0.05 wt % and 95 wt %, relative to the total weight of the solubilizing system, preferably between 0.08 wt % and 50 wt %. The pH of the solubilizing system is between 2 and 11. The micelles have a spherical, ellipsoid, cylinder or bilayers shape. Preferably, the micelles have a spherical or cylindrical shape.

According to a preferred embodiment, the perfuming or flavoring ingredient-containing oil comprises perfuming or flavoring ingredients being an aldehyde of formula $R^1CH(O)$ or a ketone of formula $(R^1)(R^2)C(=O)$ wherein $R^1$ and $R^2$ have the same meaning as above. More preferably, $R^1$ of the surfactant and $R^1$ of the perfuming or flavoring aldehyde or ketone and $R^2$ of the surfactant and $R^2$ of the perfuming or flavoring ketone are identical.

As mentioned above, the invention concerns the use of a compound of formula (I) as a delivery system to release active volatile aldehydes or ketones. In other words, it concerns a method or a process to confer, enhance, improve or modify the odor or taste properties of a perfuming or flavoring composition or of a perfumed or flavored article or of a surface, which method comprises adding to said composition or article an effective amount of at least a compound of formula (I), e.g. to release active volatile aldehydes or ketones imparting their typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in perfumery or flavor industry.

Said compositions, which in fact can be advantageously employed as perfuming or flavoring ingredients, are also an object of the present invention.

Therefore, another object of the present invention is a perfuming or flavoring composition comprising:
i) as perfuming or flavoring ingredient, at least one of the invention's compound and/or a solubilizing system as defined above;
ii) at least one ingredient selected from the group consisting of a perfumery or flavor carrier, a perfuming or flavoring co-ingredient and mixtures thereof; and
iii) optionally at least one perfumery or flavor adjuvant.

By "perfumery or flavor carrier" we mean here a material which is practically neutral from a perfumery or flavor point of view, i.e. that does not significantly alter the organoleptic properties of perfuming or flavoring ingredients. Said carrier may be a liquid or a solid.

As liquid carriers one may cite, as non-limiting examples, an emulsifying system, i.e. a solvent and a surfactant system, or a solvent commonly used in perfumery or flavor. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, triethyl citrate or mixtures thereof, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF). A detailed description of the nature and type of solvents commonly used in flavor cannot be exhaustive. Suitable solvents include, for instance, propylene glycol, triacetine, triethyl citrate, benzylic alcohol, ethanol, vegetable oils or terpenes.

As solid carrier it is meant a material where the perfuming or flavoring composition or some element of the perfuming or flavoring composition can be chemically or physically bound. In general such solid carriers are employed either to stabilize the composition, either to control the rate of evaporation of the compositions or of some ingredients. The employment of solid carriers is of current use in the art and a person skilled in the art knows how to reach the desired effect. However by way of non-limiting examples as solid carriers one may cite absorbing gums or polymers or inorganic material, such as porous polymers, cyclodextrins, wood based materials, organic or inorganic gels, clays, gypsum talc or zeolites.

As other non-limiting examples of solid carriers one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique. As non-limiting examples one may cite in particular the core-shell encapsulation with resins of the aminoplast, polyamide, polyester, polyurea or polyurethane type or a mixture thereof (all of said resins are well known to a person skilled in the art) using techniques like phase separation process induced by polymerization, by interfacial polymerization, by coacervation or altogether (all of said techniques are have been described in the prior art), and optionally in presence of polymeric stabilizer or a cationic copolymer.

In particular, as resins one may cite the ones produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cy mel® (origin: Cytec Technology Corp.), Urecoll® or Luracoll® (origin: BASF).

In particular, as resins one may cite the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins, with aldehydes is represented by articles such as those by K. Dietrich et al., *Acta Polymerica* 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinency, which also address the suitable uses of such microcapsules, are represented for example by the article of H. Y. Lee et al., *Journal of Microencapsulation*, 2002, vol. 19, pages 559-569, international patent publication WO 01/41915 or yet the article of S. Bône et al., *Chimia*, 2011, vol. 65, pages 177-181.

By "perfuming or flavoring co-ingredient" it is meant here a compound, which is used in a perfuming or flavoring preparation or a composition to impart a hedonic effect. In other words such a co-ingredient, to be considered as being a perfuming or flavoring one, must be recognized by a person skilled in the art as being able to impart or modify in a positive or pleasant way the odor or taste of a composition, and not just as having an odor or taste.

The nature and type of the perfuming or flavoring co-ingredients present in the composition do not warrant a more detailed description here, which in any case would not be exhaustive, the skilled person being able to select them on the basis of his general knowledge and according to intended use or application and the desired organoleptic effect. In general terms, these perfuming or flavoring co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming or flavoring co-ingredients can be of natural or synthetic origin.

In particular one may cite perfuming co-ingredients which are commonly used in perfume formulations, such as:
  Aldehydic ingredients: decanal, dodecanal, 2-methyl-undecanal, 10-undecenal, octanal and/or nonenal;
  Aromatic-herbal ingredients: eucalyptus oil, camphor, eucalyptol, menthol and/or alpha-pinene;
  Balsamic ingredients: coumarine, ethylvanillin and/or vanillin;
  Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;
  Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4- methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;

Fruity ingredients: gamma-undecalactone, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphthalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

The perfuming or flavoring co-ingredients to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery and flavors. It is also understood that said co-ingredients may also be compounds known to release in a controlled manner various types of perfuming or flavoring compounds.

By "perfumery or flavor adjuvant" we mean here an ingredient capable of imparting additional added benefit such as a color, a particular light resistance, chemical stability, etc. A detailed description of the nature and type of adjuvant commonly used in perfuming or flavoring compositions cannot be exhaustive, but it has to be mentioned that said ingredients are well known to a person skilled in the art. However, one may cite as specific non-limiting examples of perfumery adjuvant the following: viscosity agents (e.g. surfactants, thickeners, gelling and/or rheology modifiers), stabilizing agents (e.g. preservatives, antioxidant, heat/light and or buffers or chelating agents, such as BHT), color agents (e.g. dyes and/or pigments), preservative (e.g. antibacterial or antimicrobial or antifungal or anti irritant agents), abrasives, skin cooling agents, fixatives, insect repellents, ointments, vitamins and mixture thereof.

It is understood that a person skilled in the art is perfectly able to design optimal formulations for the desired effect by admixing the above mentioned components of a perfuming or flavoring composition, simply by applying the standard knowledge of the art as well as by trial and error methodologies.

An invention's composition consisting of at least one compound of formula (I) and at least one perfumery or flavor carrier represents a particular embodiment of the invention as well as a perfuming or flavoring composition comprising at least one compound of formula (I), at least one perfumery or flavor carrier, at least one perfuming or flavoring co-ingredient, and optionally at least one perfumery or flavor adjuvant.

It is useful to mention here that it is important to have the possibility, in the compositions mentioned above, more than one compound of formula (I) as it enables the perfumer or flavorist to prepare accords, perfumes, flavors possessing the odor or taste tonality of various compounds of the invention, creating thus new tools for his/her work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming or flavoring composition according to the invention as far as said mixture does not provide the inventive compound in a suitable form for perfumery or flavor. Thus, unpurified reaction mixtures are generally excluded from the present invention unless otherwise specified.

Furthermore, the invention's compound or invention's solubilizing system can also be advantageously used in all the fields of flavor or modern perfumery, i.e. fine or functional perfumery, to positively impart or modify the odor of a consumer product into which said compound (I) is added. Consequently, another object of the present invention is represented by a perfuming or flavoring consumer product comprising, as a perfuming or flavoring ingredient, at least one compound of formula (I) and/or a solubilizing system as defined above.

The invention's compound or solubilizing system can be added as such or as part of an invention's perfuming or flavoring composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a splash or eau de perfume, a cologne or a shave or after-shave lotion; a fabric care product, such as a liquid or solid detergent, a fabric softener, a fabric refresher, an ironing water, a paper, or a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or an antiperspirant (e.g. a spray or a roll on product), a hair remover, a tanning or a sun or an after sun product, a nail product, a skin cleansing product, a makeup); or a skin-care product (e.g. a perfumed soap, a shower or bath mousse, oil or gel, or a hygiene product or a foot/hand care product); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnish care product, a wipe, a dish detergent or a hard-surface (e.g. a floor, bath, sanitary or a window-cleaning) detergent; a leather care product; a car care product, such as a polish, a wax or a plastic cleaner.

For the sake of clarity, flavoring consumer products are edible products which may be foods or beverages and which can be fried or not, as well as frozen or not, low fat or not, marinated, battered, chilled, dehydrated, instant, canned, reconstituted, retorted or preserved. Therefore, a flavored article according to the invention comprises one or more compounds according to formula (I) or invention's solubilizing system, as well as optional benefit agents, corresponding to taste and flavor profile of the desired edible product, e.g. a savory cube.

The nature and type of the constituents of the foodstuffs or beverages do not warrant a more detailed description here, the skilled person being able to select them on the basis of his general knowledge and according to the nature of said product.

Typical examples of said flavoring consumer product include:
- seasonings or condiments, such as a stock, a savory cube, a powder mix, a flavored oil, a sauce (e.g. a relish, a barbecue sauce, a dressing, a gravy or a sweet and/or a sour sauce), a salad dressing or a mayonnaise;
- meat-based products, such as a poultry, beef or pork based product, a seafood, surimi, or a fish sausage;
- soups, such as a clear soup, a cream soup, a chicken or beef soup or a tomato or asparagus soup;
- carbohydrate-based products, such as instant noodles, rice, pasta, potatoes flakes or fried noodles, pizza, tortillas, wraps;
- dairy or fat products, such as a spread, a cheese, or regular or low fat margarine, a butter/margarine blend, a butter, a peanut butter, a shortening, a processed or flavored cheese;
- savory products, such as a snack, a biscuit (e.g. chips or crisps) or an egg product, a potato/tortilla chip, a microwave popcorn, nuts, a bretzel, a rice cake, a rice cracker, etc;
- imitation products, such as a dairy (e.g a reformed cheese made from oils, fats and thickeners) or seafood or meat (e.g. a vegetarian meat replacer, a veggie burger) or analogues;
- pet or animal food; or
- beverages (ready-to-drink or powder soft).

Particularly preferred flavoring consumer products, in which the compound according to formula (I) or invention's solubilizing system finds utility, include beverages.

The proportions in which the compounds according to the invention or the invention's solubilizing system can be incorporated into the various of the aforementioned products or compositions vary within a wide range of values. These values are dependent on the nature of the article to be perfumed or flavored and on the desired organoleptic effect as well as the nature of the co-ingredients in a given base when the compounds according to the invention are mixed with perfuming or flavoring co-ingredients, solvents or additives commonly used in the art.

For example, in the case of perfuming compositions, typical concentrations are in the order of 0.001% to 30% by weight, or even more, of the compounds of the invention based on the weight of the composition into which they are incorporated. Concentrations lower than these, such as in the order of 0.01% to 5% by weight, can be used when these compounds are incorporated into perfuming consumer products, percentage being relative to the weight of the article.

In the case of flavoring compositions, typical concentrations are in the order of 0.05% to 30%, more preferably 0.1% to 20%, most preferably 0.1% to 10%, of the compounds of the invention based on the weight of the flavoring compositions into which they are incorporated. Concentrations lower than these, such as in the order of 0.5 ppm to 300 ppm by weight, more preferably 5 ppm to 75 ppm, most preferably 8 to 50 ppm, can be used when these compounds are incorporated into flavored articles, the percentage being relative to the total weight of the article.

The compounds of the present invention can be prepared by the condensation of the Q-L-$NH_2$ part with a perfuming or flavoring aldehyde or ketone of formula $R^1C(O)R^2$. The skilled person in the art will be able to select the suitable conditions to perform said condensation. The Q-L-$NH_2$ is commercially available or is synthesized as defined below.

In an aqueous base compound of formula (III); i.e. Q-L-$NH_2$ and flavor or fragrance aldehyde of formula ($R^1$)CHO or a flavor or fragrance ketone of formula ($R^1$)($R^2$)CO are in equilibrium with a compound of formula (I) to form a dynamic mixture. Said dynamic mixture, obtainable by combining, in the presence of water, at least a primary amine of formula (III) with at least one perfuming or flavoring aldehyde and/or ketone is a valuable perfuming or flavoring ingredient capable of releasing, in a controlled and prolonged manner, said perfuming or flavoring aldehydes and/or ketones and, at the same time, giving a more evenly distributed effect with mixtures of aldehydes and/or ketones. The invention's dynamic mixture enables a controlled release of one or several perfuming or flavoring compounds. The structure of the compound of formula (I) is chosen in a way as to stabilize the imine bond by forming a micelle or a vesicle and thus to shift the equilibrium towards the formation of the imine bond.

Such a behavior makes the invention's dynamic mixture particularly suitable as perfuming or flavoring ingredient. Consequently, the use of an invention's dynamic mixture as perfuming or flavoring ingredient is an object of the present invention. In particular it concerns a method to confer, enhance, improve or modify the odor properties of a perfuming or flavoring composition or of a perfumed or flavored article, which method comprises adding to said composition or article an effective amount of an invention's dynamic mixture.

So, a last object of the invention is a use as perfuming or flavoring ingredient of a dynamic mixture, for the controlled release of perfuming or flavoring aldehydes and/or ketones, obtainable by reacting, in a water-containing medium,
i) at least one flavor or fragrance aldehyde of formula ($R^1$)CHO or a flavor or fragrance ketone of formula ($R^1$)($R^2$)CO as defined above;

with ii) at least one derivative of formula $$Q\text{-}L\text{-}NH_2 \quad (IV)$$

wherein:

Q and L have the same meaning as above.

As "dynamic mixture" we mean here a composition comprising a solvent (e.g. a water-containing medium), several starting components as well as several addition products that are the result of reversible reactions between the various starting components. It is believed that said dynamic mixtures take advantage from reversible chemical reactions, in particular from the formation and dissociation by reversible condensation between the carbonyl group of the perfuming or flavoring aldehyde or ketone and the two $NH_2$ moieties of the compound of formula (IV). The ratio between the various starting and addition products depends on the equilibrium constant of each possible reaction between the starting components. The usefulness of said "dynamic mixture" derives from a synergistic effect between all the components.

The dynamic mixture is obtained by reacting one or more of the invention's primary amines of formula (IV) with one or more perfuming or flavoring ingredients in a water-containing medium. By "water-containing medium" we mean here a dispersing medium comprising at least 10% w/w, or even 30% w/w, of water and optionally an aliphatic alcohol such as a $C_1$ to $C_3$ alcohol, for example ethanol. More preferably, said medium comprises at least 50% w/w, or even 70%, water optionally containing up to 30% of a surfactant. According to a particular embodiment of the invention, the water-containing medium may have a pH comprised between 2 and 11, and in particular between 3 and 10. As the primary amine according to the present invention act as bases, they might increase the pH of the medium in which they are intended to be used. The pH of the medium can be re-adjusted (to be acidic) by adding an acid. The nature and type of the acid do not warrant a more detailed description here, which in any case would not be exhaustive, the skilled person being able to select them on the basis of its general knowledge and according to intended use or application. As examples for some of the preferred acids, one might cite mineral acids such as hydrochloric acid, phosphoric acid or sulfuric acid, or organic acids such as formic acid, acetic acid or citric acid.

The invention's dynamic mixture can be obtained by admixing together, in the presence of water, at least one of the invention's primary amine of formula (IV) and at least one perfuming or flavoring aldehyde or ketone. It is very frequent in the perfumery or flavor art to admix together several perfuming or flavoring ingredients to achieve a more pleasant and natural scent. However, it must be considered that every single compound present in a dynamic mixture may influence the overall equilibrium and therefore the evaporation of every single perfuming or flavoring ingredient. Under such circumstances, one could have expected that the presence of several compounds capable of reacting all together (each of them with different stabilities and reactivities), could have easily led to a negative impact of the release of the individual perfuming or flavoring aldehyde or ketone. This could result in a negative hedonic effect, or at least (and in the best case) that only some particular perfuming or flavoring ingredients would be boosted, resulting in any case in a modification of the olfactive profile of the perfume or flavor over time, which is obviously an undesired result. Now, to the contrary of the expectation and very surprisingly, we found that the use of a diamine according to the present invention provides a general improvement of performance of all aldehydes and ketones in a mixture and that this improved performance is more evenly distributed between the different carbonyl compounds in the mixture.

Therefore, in all the aspects of the above-described invention, a dynamic mixture obtained by reacting together at least one compound of formula (IV) with at least one, or even more, perfuming or flavoring compounds is particularly appreciated. Similarly, in all the aspects of the above-described invention, it is also particularly appreciated to obtain a dynamic mixture by reacting together at least one or two compound of formula (IV) with at least one, or more, perfuming or flavoring compounds.

As mentioned above, the invention's dynamic mixture comprises several starting components that may react, in a reversible manner, between them to form addition products.

Now, a further aspect of the present invention concerns the dynamic mixtures themselves. Indeed, the above-mentioned dynamic mixtures are also new, and therefore represent another object of the invention. So another aspect of the present invention are the dynamic mixtures as such, useful for the controlled release of perfuming or flavoring aldehydes or ketones. In particular said dynamic mixture are consisting of the aqueous medium, in particular water at an appropriate pH, the invention's amine of formula (IV), the perfuming or flavoring compound and the reaction product of said last two ingredients.

It is believed that the main components of the dynamic mixture are the free aldehyde and/or ketone, the primary amine of formula (IV) and the resulting addition products (such as the corresponding imine compound of formula (I)). A specific example of such a mixture and equilibrium is presented in Scheme (I):

Scheme (I):

Example of an equilibrium and the species present in a dynamic mixture obtained from one specific aldehyde and one specific amine derivative or from the corresponding imine derivative

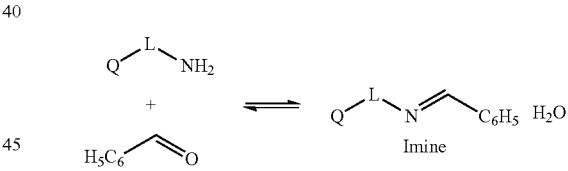

As a consequence of the fact that the reactions are reversible, a dynamic mixture can also be obtained by adding several imine derivatives, or by adding one imine derivative and one perfuming or flavoring compound into water and letting the mixture attain its equilibrium. However, it has to be pointed out that the time required to reach the equilibrium point can vary significantly depending on the fact that there is used, for instance, the invention's amine as starting material, as said time is believed to be dependent on various parameters such as solubilities or the pH of the medium.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) on a 400 or 500 MHz instrument for $^1H$ and $^{13}C$, the chemical shifts δ are indicated in ppm with respect to TMS as standard, the coupling constants J are expressed in Hz. The polymers used for the preparation of the compounds according to formula (I) are not monodisperse. According to the data sheets of the producers, the following average structures were considered: 2,5,8,11,14,17,20,23,26,29,32-undecaoxatetratriacontan-34-ol [$CH_3(OCH_2CH_2)_{11}OH$, PEG11], Jeffamine® M-600 [$CH_3OCH_2CH_2(OCH_2CHCH_3)_9NH_2$], Jeffamine® M-1000 [$CH_3(OCH_2CH_2)_{19}(OCH_2CHCH_3)_3NH_2$] and Jeffamine® M-2070 [$CH_3 (OCH_2CH_2)_{31} (OCH_2CHCH_3)_{10} NH_2$].

Example 1

Synthesis of Non-Commercially Starting Material
  a) Synthesis of Non-Commercially Available Amines of Structure Q-L-NH$_2$ Synthesis of 2-(4-((2,5,8,11,14,17,20,23,26,29,32-undecaoxatetratriacontan-34-yl)oxy)phenyl)ethan-1-amine (PEG$_{11}$-Tyramine)

2,5,8,11,14,17,20,23,26,29,32-Undecaoxatetratriacontan-34-ol (PEG$_{11}$, 1 eq., average structure) was dissolved in pyridine (1 mL for 1 g of PEG$_{11}$) at 0° C. A solution of tosyl chloride (3.6 eq.) in pyridine (0.3 mL for 1 mmol of tosyl chloride) was then added slowly at −5° C. The mixture was stirred for 4 to 48 h at 0° C., and treated by adding ice with 6 N HCl (5 mL for 1 mL of the total volume of pyridine). The mixture was extracted three times with $CH_2Cl_2$ (3 mL for 1 mL of aqueous solution) and the organic layer was washed with 2 N HCl (1 mL for 3 mL of organic solution). The organic layer was dried with magnesium sulfate and evaporated to provide the pure tosylated compound (PEG$_{11}$-Tos) as a clear yellow oil.

$^1$H NMR (CDCl$_3$, 400 MHz): δ=7.76 (d, J=8.4 Hz, 2H), 7.30 (d, J=8.3 Hz, 2H), 4.12 (t, J=4.8 Hz, 2H), 3.64 (t, J=5.0 Hz, 2H), 3.62 (m, 6H), 3.60 (m, 24H), 3.57 (m, 4H), 3.54 (m, 4H), 3.51 (m, 2H), 3.34 (s, 3H), 2.41 (s, 3H).

$^{13}$C NMR (CDCl$_3$, 400 MHz, 25° C.): δ=144.77, 133.02, 129.82, 127.96, 71.92, 70.72, 70.55, 70.49, 69.25, 68.67, 59.01, 21.63.

tert-Butyl (4-hydroxyphenethyl)carbamate (1.0 g, 1 eq., 4.216 mmol) was dissolved in acetonitrile (10 mL for 1 g of PEG$_{11}$-Tos) and the solution was heated up to reflux. Potassium carbonate (932 mg, 1.6 eq., 6.746 mg) was then added followed by PEG$_{11}$-Tos (2.757 g, 1 eq., 4.216 mmol). The mixture was stirred for 12 h at reflux. The solvent was then evaporated, $CH_2Cl_2$ (100 mL) was added and the solution was filtered. The aqueous mixture was washed three times with a saturated aqueous solution of NaHCO$_3$ (20 mL). The resulting organic phase was then dried with sodium sulfate and further evaporation under reduced pressure afforded pure tert-butyl (4-((2,5,8,11,14,17,20,23,26,29,32-undecaoxatetratriacontan-34-yl)oxy)phenethyl)carbamate (2.820 g, 91%).

$^1$H NMR (CDCl$_3$, 400 MHz): δ=7.08 (d, J=8.6 Hz, 2H), 6.85 (d, J=8.6 Hz, 2H), 4.53 (s, 1H), 4.10 (t, J=5.0 Hz, 2H), 3.84 (t, J=5.0 Hz, 2H), 3.77-3.50 (m, 40H), 3.37 (s, 3H), 3.35-3.26 (m, 2H), 2.72 (t, J=6.9 Hz, 2H), 1.43 (s, 9H).

$^{13}$C NMR (CDCl$_3$, 400 MHz): δ=156.86, 155.36, 130.80, 129.12, 114.16, 71.39, 70.24, 70.07, 70.03, 69.93, 69.19, 66.94, 58.36, 41.55, 34.79, 27.94.

tert-Butyl (4-((2,5,8,11,14,17,20,23,26,29,32-undecaoxatetratriacontan-34-yl)oxy)phenethyl)carbamate (2.000 g) was dissolved in a mixture of $CH_2Cl_2$ and TFA (3:1.50 mL) and stirred at room temperature. After 2 h, the mixture was evaporated, $CH_2Cl_2$ (100 mL) was added and the solution was washed with a saturated aqueous solution of NaHCO$_3$ (3×20 mL). The solution was dried with sodium sulfate and further evaporation under reduced pressure afforded pure 2-(4-((2,5,8,11,14,17,20,23,26,29,32-undecaoxatetratriacontan-34-yl)oxy)phenyl)ethan-1-amine (PEG$_{11}$-Tyramine, 1.228 g, 87%).

$^1$H NMR (CDCl$_3$, 400 MHz): δ=7.10 (d, J=8.6 Hz, 2H), 6.85 (d, J=8.6 Hz, 2H), 4.11 (t, J=5.0 Hz, 2H), 3.84 (t, J=5.0 Hz, 2H), 3.76-3.50 (m, 40H), 3.37 (s, 3H), 2.96 (t, J=7.1 Hz, 2H), 2.71 (d, J=7.1 Hz, 2H).

$^{13}$C NMR (CDCl$_3$, 400 MHz): δ=157.01, 131.68, 129.40, 114.39, 71.65, 70.52, 70.34, 70.31, 70.29, 70.21, 69.49, 67.21, 58.70, 43.34, 38.58.

b) Synthesis of Non-Commercially Available Reference Amines of Structure Q-NH$_2$ Synthesis of 2,5,8,11,14,17,20,23,26,29,32-undecaoxatetratriacontan-34-amine (PEG$_{11}$-Amine)

Phtalimide (0.8775 g, 1.4 eq.) was dissolved in acetonitrile (30 mL for 1 g of phtalimide) and the solution was heated to reflux. Potassium carbonate (0.9421 g, 1.6 eq.) was added, followed by the PEG$_{11}$-Tos (prepared as described above, 3.000 g, 1.0 eq.). The mixture was stirred for 12 h at reflux. The solvent was then evaporated and water was added (10 mL for Ig of PEG$_{11}$-Tos). The aqueous mixture was extracted three times with $CH_2Cl_2$ (3 mL for 1 mL of aqueous solution). The resulting organic phase was then washed with a saturated sodium carbonate solution (1 mL for 3 mL of organic solution), dried with magnesium sulfate and further evaporation under reduced pressure afforded pure 2-(2,5,8,11,14,17,20,23,26,29,32-undecaoxatetratriacontan-34-yl)isoindoline-1,3-dione (1.981 g, 72%).

$^1$H NMR (CDCl$_3$, 400 MHz): δ=7.83 (m, 2H), 7.70 (m, 2H), 3.88 (t, J=5.8 Hz, 2H), 3.73 (t, J=5.8 Hz, 2H), 3.63 (m, 40H), 3.37 (s, 3H).

$^{13}$C NMR (CDCl$_3$, 400 MHz): δ=168.24, 133.92, 132.14, 123.24, 71.94, 70.57, 70.09, 67.92, 59.05, 37.28.

2-(2,5,8,11,14,17,20,23,26,29,32-Undecaoxatetratriacontan-34-yl)isoindoline-1,3-dione (1 eq.) was dissolved in THF (30 mL for 1 g) and aqueous hydrazine (40 eq.) was added. The mixture was stirred for 4 h at room temperature. The solvent was evaporated and water was added (10 mL for 1 g). The aqueous phase was extracted CHCl$_3$ (3×, 3 mL for 1 mL of aqueous solution) and the combined organic layers were dried with magnesium sulphate. Further evaporation under reduced pressure afforded pure 2,5,8,11,14,17,20,23,26,29,32-undecaoxatetratriacontan-34-amine (PEG$_1$-Amine, 76%) as yellow-brown oil.

$^1$H NMR (CDCl$_3$, 400 MHz): δ=3.64 (m, 40H), 3.52 (m, 2H), 3.37 (s, 3H); 2.89 (t, J=4.8 Hz, 2H).

$^{13}$C NMR (CDCl$_3$, 400 MHz): δ=72.9, 72.0, 70.05, 70.06, 70.3, 59.0, 41.7.

Example 2

Synthesis of Cleavable Imine Surfactants According to Formula (I) with a Total HLB Value Comprised Between 3 and 18

General Procedure A:
  A flavor or fragrance aldehyde (1 eq.) and an amine derivative of the formula Q-L-NH$_2$ (1.2 eq.) were dissolved in CHCl$_3$ (2 mL for 1 g of amine) at room temperature under argon. Sodium sulphate was added and the mixture was stirred for 1 to 3 weeks, until the conversion has reached at least 95%. The solvent was evaporated under vacuum for several days to remove the remaining water and reach full conversion, providing an imine according to formula (I) (95-99%).

(a) Condensation of PEG$_{11}$-Tyramine with hexylcinnamic aldehyde according to the General Procedure A afforded the corresponding imine (Imine A).

$^1$H NMR (CDCl$_3$, 400 MHz): δ=7.74 (s, 1H), 7.44-6.75 (m, 5H), 7.12 (d, J=8.6 Hz, 2H), 6.83 (d, J=8.6 Hz, 2H), 6.67 (s, 1H), 4.10 (t, J=5.0 Hz, 2H), 3.82 (t, J=5.0 Hz, 2H), 3.78-3.47 (m, 42H), 3.37 (s, 3H), 3.01-2.84 (m, 2H), 2.65-2.39 (m, 2H), 1.59-1.50 (m, 2H), 1.44-1.18 (m, 6H), 0.88 (t, J=6.9 Hz, 3H).

ESI-MS: calculated for C$_{46}$H$_{75}$NO$_{12}$ [M+H]$^+$: 834.53, found: 834.85.

(b) Condensation of Jeffamine® M-1000 with hexylcinnamic aldehyde according to the General Procedure A afforded the corresponding imine (Imine B).

$^1$H NMR (CDCl$_3$, 400 MHz): δ=8.14 (cis, s, 0.1H), 7.83 (trans, s, 0.9H), 7.29-7.15 (m, 5H), 6.81 (cis, s, 0.1H), 6.63 (trans, s, 0.9H), 3.75-3.25 (m, 88H), 3.29 (s, 3H), 2.51 (t, J=8.0 Hz, 2H), 1.50-1.42 (m, 2H), 1.31-1.15 (m, 6H), 1.13-0.99 (m, 9H), 0.79 (t, J=6.9 Hz, 3H).

ESI-MS: calculated for C$_{63}$H$_{117}$NO$_{22}$ [M+H]$^+$: 1240.81, found: 1240.92.

(c) Condensation of Jeffamine® M-2070 with hexylcinnamic aldehyde according to the General Procedure A afforded the corresponding imine (Imine C).

$^1$H NMR (CDCl$_3$, 400 MHz): δ=8.14 (cis, s, 0.1H), 7.83 (trans, s, 0.9H), 7.43-7.11 (m, 5H), 6.81 (cis, s, 0.1H), 6.62 (trans, s, 0.9H), 3.85-3.14 (m, 150H), 3.29 (s, 3H), 2.51 (t, J=8.0 Hz, 2H), 1.53-1.37 (m, 2H), 1.34-1.13 (m, 8H), 1.13-0.98 (m, 30H), 0.79 (t, J=6.7 Hz, 3H).

(d) Condensation of Jeffamine® M-1000 with citral according to the General Procedure A afforded the corresponding imine (Imine D).

$^1$H NMR (CDCl$_3$, 400 MHz): δ=8.20 (d, J=9.3 Hz, 0.5H), 8.15 (d, J=9.3 Hz, 0.5H), 6.03-5.91 (m, 1H), 5.21-4.96 (m, 1H), 3.82-3.23 (m, 85H), 3.36 (s, 3H), 2.36-2.02 (m, 4H), 1.89 (s, 1.5H), 1.85 (d, J=1.4 Hz, 1.5H), 1.66 (s, 3H), 1.61-1.55 (m, 3H), 1.19-0.97 (m, 9H).

ESI-MS: calculated for C$_{58}$H$_{113}$NO$_{22}$ [M+H]$^+$: 1176.78, found: 1176.94.

This imine was alternatively prepared according to the General Procedures B and D (see below).

(e) Condensation of Jeffamine® M-2070 with citral according to the General Procedure A afforded the corresponding imine (Imine E).

$^1$H NMR (CDCl$_3$, 400 MHz): δ=8.19 (d, J=9.3 Hz, 0.5H), 8.13 (d, J=9.3 Hz, 0.5H), 6.03-5.93 (m, 1H), 5.15-5.02 (m, 1H), 3.82-3.23 (m, 150H), 3.36 (s, 3H), 2.37-1.98 (m, 4H), 1.90 (s, 1.5H), 1.85 (d, J=1.4 Hz, 1.5H), 1.66 (s, 3H), 1.61-1.53 (m, 3H), 1.21-1.00 (m, 30H).

This imine was alternatively prepared according to the General Procedure D (see below).

(f) Condensation of PEG$_{11}$-Tyramine with citral according to the General Procedure A afforded the corresponding imine (Imine I).

ESI-MS: calculated for C$_{41}$H$_{71}$NO$_{12}$ [M+H]$^+$: 770.50, found: 770.67.

General Procedure B:

A flavor or fragrance aldehyde (1-1.1 eq.) was added to an amine derivative of the formula Q-X-L-NH$_2$ (1 eq.). The reaction mixture was heated to 80-100° C. Then vacuum (8 mbar) was applied and the mixture stirred at 80-100° C. for 4-7 h, before being cooled to room temperature. NMR analysis showed that the samples typically contained some unreacted amine.

(g) Condensation of Jeffamine® M-1000 with (Z)-4-dodecenal according to the General Procedure B afforded the corresponding imine (Imine F).

$^1$H NMR (CDCl$_3$, 500 MHz): δ=7.78-7.75 (m, 0.2H), 7.70-7.63 (m, 0.8H), 5.45-5.28 (m, 2H), 3.82-3.05 (m, 85H), 2.32-2.10 (m, 4H), 2.02 (q, J=6.7 Hz, 2H), 1.40-1.00 (m, 19H), 0.88 (t, J=6.9 Hz, 3H).

(h) Condensation of Jeffamine® M-2070 with (Z)-4-dodecenal according to the General Procedure B afforded the corresponding imine (Imine G).

$^1$H NMR (CDCl$_3$, 500 MHz): δ=7.78-7.72 (m, 0.2H), 7.70-7.61 (m, 0.8H), 5.46-5.27 (m, 2H), 3.85-3.20 (m, 220H), 2.32-2.19 (m, 4H), 2.02 (q, J=6.5 Hz, 2H), 1.40-1.20 (m, 15H), 1.20-1.05 (m, 40H), 0.88 (t, J=6.8 Hz, 3H).

General Procedure C:

A flavor or fragrance aldehyde (1 eq.) and an amine (1.2 eq.) were dissolved in CHCl$_3$ (2 mL for 1 g of amine) at room temperature. The mixture was stirred for 1 to 2 d. Then the solvent was evaporated under reduced pressure for several days to remove the remaining water and reach full conversion, providing ready-to-use imines (98-100%).

(i) Condensation of Jeffamine® M-1000 with benzaldehyde according to the General Procedure C afforded the corresponding imine (Imine H).

$^1$H NMR (CDCl$_3$, 400 MHz): δ=8.29 (s, trans, 0.5H), 8.28 (s, cis, 0.5H), 7.75-7.65 (m, 2H), 7.42-7.32 (m, 3H), 3.86-3.03 (m, 88H), 1.28-0.92 (m, 9H).

General Procedure D:

A flavor or fragrance aldehyde (1 eq.) and an amine (1 eq.) were dissolved in CHCl$_3$ (ca. 32 mL for 1 g of aldehyde) and heated under reflux (55° C.) for 18-24 h with azeotropic removal of water (Dean-Stark apparatus). Then the solvent was evaporated under reduced pressure, providing ready-to-use imines.

According to the equation (1) and the reference X. Guo, Z. Rong and X. Ying, *Journal of Colloid and Interface Science* 2006, vol. 298, pages 441-450 the following HLB values were calculated using ECL method described above for the different imines of formula (I). The values are reported in Table 2.

TABLE 1

Calculated HLB values with ECL method for compounds according to formula (I)

| Compound of formula (I) | HLB (Q) | HLB (L) | HLB (A) | HLB$_{total}$ |
|---|---|---|---|---|
| Imine A | 10.00 | −2.43 | −3.31 | 11.26 |
| Imine B [a)] | 12.01 | −2.28 | −3.31 | 13.41 |
| Imine C | 13.55 | −4.44 | −3.31 | 12.79 |
| Imine D | 12.01 | −2.28 | −2.23 | 14.49 |
| Imine E | 13.55 | −4.44 | −2.23 | 13.87 |
| Imine F | 12.01 | −2.28 | −3.08 | 13.64 |
| Imine G | 13.55 | −4.44 | −3.08 | 13.02 |
| Imine H | 12.01 | −2.28 | −0.41 | 17.13 |
| Imine I | 10.00306 | −2.4332 | −2.2322 | 12.33766 |

[a)] Example of calculation of HLB by using ECL method for Imine B:
Q = 1CH$_3$ + 19EO
L = 3PO
A = 1N + 5CH$_2$ + phenyl + 2CH + 1C (considered as CH) + 1CH$_3$
$N_{EO}^{eff}$ = 13.45 * ln(19) − 0.16 * 19 + 1.26 = 37.82
$N_{PO}^{eff}$ = 2.057 * 3 + 9.06 = 15.231
$N_{CH_2}^{eff}$ = 0.965 * 5 − 0.178 = 4.647
HLB(Q) = −0.48 + 0.33*37.82 = 12.006
HLB(L) = −0.15*15.231 = −2.284
HLB(A) = 2.4 − 0.48*4.647 − 1.60 − 0.48*4 = −3.308
HLB = 7 + (12.006 − 2.284 − 3.308) = 13.413

Example 3

Comparative Example a) Synthesis of Cleavable Imine Surfactants According to Formula (I) with a Total HLB Value Below 3 or Above 18
(a) Condensation of Jeffamine® M-1000 with vanillin according to the General Procedure C afforded the corresponding imine (Imine C1).

$^1$H NMR (CDCl$_3$, 400 MHz): δ=8.19 (s, 0.5H), 8.18 (s, 0.5H), 7.40 (m, 1H), 7.10 (dd, J=8.0, 1.8 Hz, 1H), 6.91 (d, J=8.0 Hz, 1H), 3.94 (s, 3H), 3.78-3.12 (m, 85H), 3.37 (s, 3H), 1.27-1.00 (m, 9H).

This imine was alternatively prepared according to the General Procedure D.

(b) Condensation of Jeffamine® M-600 with hexylcinnamic aldehyde according to the General Procedure a afforded the corresponding imine (Imine C2).

$^1$H NMR (CDCl$_3$, 400 MHz): δ=8.21 (cis, s, 0.1H), 7.90 (trans, s, 0.9H), 7.39-7.22 (m, 5H), 6.88 (cis, s, 0.1H), 6.69 (trans, s, 0.9H), 3.68-3.27 (m, 40H), 3.34 (s, 3H), 2.58 (t, J=7.7 Hz, 2H), 1.60-1.44 (m, 2H), 1.37-1.21 (m, 6H), 1.21-1.05 (m, 27H), 0.85 (t, J=6.8 Hz, 3H).

(c) Condensation of Jeffamine® M-600 with citral according to the General Procedure A afforded the corresponding imine (Imine C3).

$^1$H NMR (CDCl$_3$, 400 MHz): δ=8.21 (d, J=9.3 Hz, 0.25H), 8.16 (d, J=9.2 Hz, 0.25H), 6.03-5.94 (m, 1H), 5.14-5.03 (m, 1H), 3.73-3.04 (m, 40H), 3.35 (s, 3H), 2.39-2.01 (m, 4H), 1.90 (s, 1.5H), 1.85 (d, J=1.4 Hz, 1.5H), 1.66 (s, 3H), 1.61-1.55 (m, 3H), 1.22-0.94 (m, 27H).

This imine was alternatively prepared according to the General Procedure D.

(d) Condensation of Jeffamine® M-600 with (Z)-4-dodecenal according to the General Procedure B afforded the corresponding imine (Imine C4).

$^1$H NMR (CDCl$_3$, 500 MHz): δ=7.78-7.72 (m, 0.2H), 7.70-7.63 (m, 0.8H), 5.46-5.27 (m, 2H), 3.77-3.20 (m, 43H), 2.32-2.09 (m, 4H), 2.02 (q, J=6.7 Hz, 2H), 1.42-1.20 (m, 14H), 1.20-1.05 (m, 34H), 0.88 (t, J=6.9 Hz, 3H).

b) Synthesis of Cleavable Imine Surfactants without Hydrophobic Linker (L), but with a Total HLB Value Comprised Between 3 and 18
(e) Condensation of PEG$_{11}$-Amine with hexylcinnamic aldehyde according to the General Procedure a afforded the corresponding imine (Imine C5).

$^1$H NMR (CDCl$_3$, 400 MHz): δ=7.91 (s, 1H), 7.43-7.20 (m, 5H), 6.73 (s, 1H), 3.78-3.51 (m, 44H), 3.38 (s, 3H), 2.58 (t, J=8.2 Hz, 2H), 1.59-1.46 (m, 2H), 1.42-1.21 (m, 6H), 0.87 (t, J=7.1 Hz, 3H).

(f) Condensation of PEG$_{11}$-Amine with citral according to the General Procedure A afforded the corresponding imine (Imine C6).

$^1$H NMR (CDCl$_3$, 400 MHz): δ=8.22 (d, J=9.4 Hz, 0.5H), 8.17 (d, J=9.4 Hz, 0.5H), 6.06-5.94 (m, 1H), 5.17-4.99 (m, 1H), 3.85-3.44 (m, 44H), 3.37 (s, 3H), 2.36-2.09 (m, 4H), 1.91 (d, J=1.3 Hz, 1.5H), 1.87 (d, J=1.3 Hz, 1.5H), 1.68 (s, 3H), 1.62-1.56 (m, 3H).

(g) Condensation of Jeffamine® M-1000 with 8-methoxy-3-phenyl-3,4-dihydro-2H-benzo[e][1,3]oxazine-6-carbaldehyde (which is not a perfuming aldehyde) according to the General Procedure D (with 20 mL of CHCl$_3$ for 0.1 g of aldehyde) afforded the corresponding imine (Imine C7 corresponding to imines reported in *Polymer* 2014, vol. 55, pages 1443-1451).

$^1$H NMR (CDCl$_3$, 500 MHz): δ=8.16 (2 s, 1H), 7.50-7.30 (m, 1H), 7.30-7.08 (m, 4H), 7.00-6.90 (m, 1H), 6.80-6.66 (m, 1H), 5.47 (s, 2H), 4.65 (s, 2H), 3.90 (s, 3H), 3.82-3.28 (m, 88H), 1.30-0.80 (m, 9H).

See: A. Van, K. Chiou and H. Ishida, *Polymer* 2014, vol. 55, pages 1443-1451.

According to the equation (1) and the reference X. Guo, Z. Rong and X. Ying, *Journal of Colloid and Interface Science* 2006, vol. 298, pages 441-450 the following HLB values were calculated using ECL method described above for the different comparative imines. The value are reported in Table 2

TABLE 2

Calculated HLB values with ECL method for reference compounds

| Compound of formula (I) | HLB (Q) | HLB (L) | HLB (A) | HLB$_{total}$ |
|---|---|---|---|---|
| Imine C1 | 12.01 | −2.28 | 2.10 | 18.83 |
| Imine C2 | −0.11 | −4.14 | −3.31 | −0.56 |
| Imine C3 | −0.11 | −4.14 | −2.23 | 0.52 |
| Imine C4 | −0.11 | −4.14 | −3.08 | −0.33 |
| Imine C5 | 10.01 | 0 | −3.31 | 13.69 |
| Imine C6 | 10.01 | 0 | −2.23 | 14.77 |
| Imine C7[a] | 12.00 | −2.28 | 2.41 | 19.31 |

[a]Example of calculation of HLB by using ECL method for Imine C7:
Q = 1CH$_3$ + 19(EO)
L = 3(PO)
A = 2N + 2Phenyl + 2O + 2CH$_2$ + 1CH + 1CH$_3$
HLB(Q) = 12.006; HLB(L) = −2.284; HLB(A) = 2.41 ⇒ HLB = 19.13

Imines C1-C4 and C7 have a HLB not comprised between 3 and 18 and Imine C5 and C6 are of formula Q-A. C7 has been reported in *Polymer* 2014, vol. 55, pages 1443—as being a surfactant. However, C7 has a HLB value indicating a strong water solubility meaning that said compound does not allow solubilizing perfuming oil contrary to imine of the present invention.

Example 4

Figure 2:
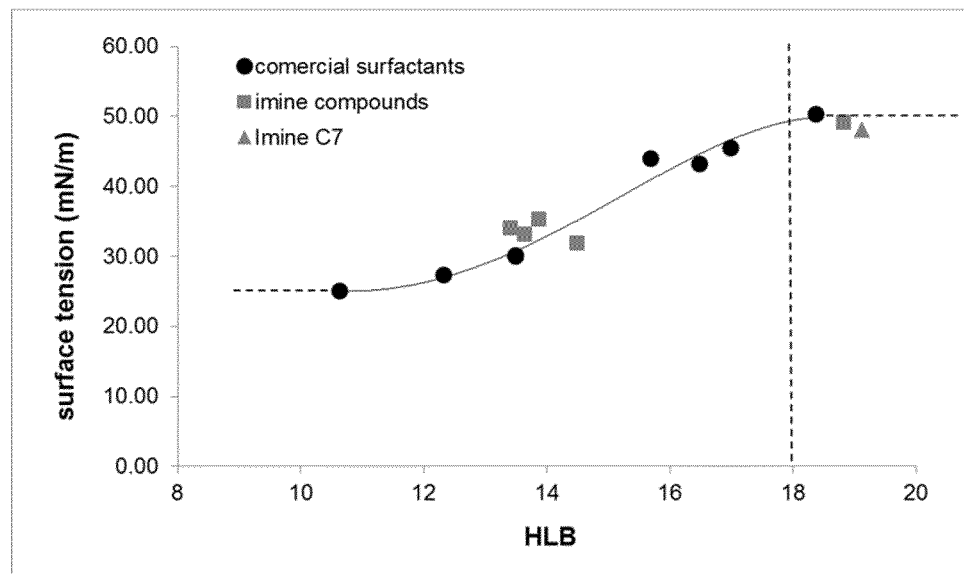
FIG. 2: The surface activity of aqueous solutions of several surfactants at concentration of 1% wt measured by Kruss DSA 10 MK2 Drop Shape Analysis System in function of the HLB value of the corresponding surfactant molecules calculated by using ECL model as reported in *Journal of Colloid and Interface Science* 2006, vol. 298, pages 441-450.

Surface Activity of Imine Surfactants. Correlation with HLB Calculated with ECL Method The surface activity of aqueous solutions of typical well known surfactants at concentration of 1% wt was measured by Kruss DSA 10 MK2 Drop Shape Analysis System. In parallel, the HLB value of the surfactant molecules was calculated by using ECL model. FIG. 2 represented the correlation between the surface tension and the calculated HLB values (black circles). The curve reached a saturation value at HLB 18, which was the limit of the HLB range for the compound of formula (I). All molecules having HLB higher than 18 are not part of the present invention due to a strong water solubility and an insufficient surface activity.

The surface tension of compounds of formula (I): Imine F, Imine D, Imine E, Imine B and of comparative Imine C1, was measured as well and the data were added to FIG. 2 (grey squares). The surface tension values of Imines: F, D, E and B confirm the strong surface activity of these molecules leading to successful solubilisation capacity. The compound Imine C1 had high surface tension value, which was positioned on the surface tension plateau. The HLB calculated for this molecule was higher than 18 and therefore out of the limits fixed in the present invention.

As a comparative example, the compound Imine C7 reported in *Polymer* 2014, vol. 55, pages 1443-1451 was synthetized (see Example 3 g)) and surface tension of the aqueous solution of 1% wt of this molecule was measured. The data was included in FIG. 2 (black triangle). The result confirms that this molecule could not be considered as a surfactant according to the HLB calculation method and solubilisation criteria.

FIG. 2 clearly show the correlation between the surface tension measured and the HLB calculated following ECL method confirming that the HLB value is a parameter allowing characterizing the surfactants.

Figure 3:
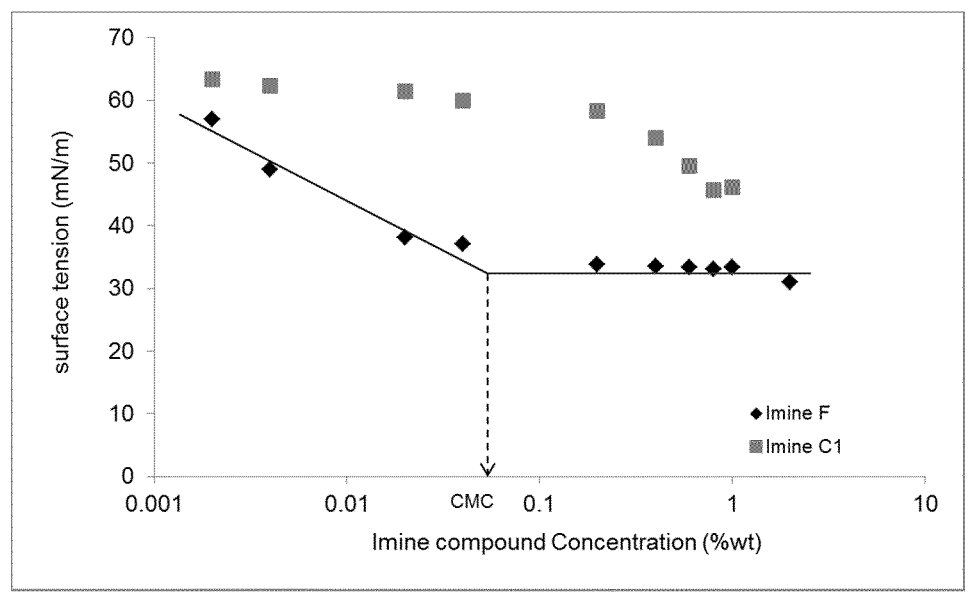
FIG. 3: The surface tension as function of the concentration for Imine compounds F and C1.

The surface tension as function of the concentration of Imine compounds F and C1 was measured and presented on FIG. 3. The curve corresponding to Imine F clearly demonstrated the existence of critical concentration (CMC) above which the surface tension had a constant value and the Imine F compound self-aggregates in micelles. The curve corresponding to Imine C1 does not follow the same trend confirming the absence of CMC and self-aggregation of this compound in micelles.

Example 5

Equilibration of Imines According to Formula (I) and of Comparative Imines in Deuterium Oxide The compounds according to formula (I) at different concentrations (c=10 . . . 500 mM) were individually dissolved in deuterium oxide (0.7 mL) at room temperature. The pD was measured and the hydrolysis of the imine was followed by $^1$H NMR until an equilibrium was reached. The imine concentration at equilibrium was determined. Reactions with constant pD were either performed at unmodified pD (basic) or in a 4-(2-hydroxyethyl)-1-piperazineethanesulfonic acid (HEPES) buffer (slightly acidic). The data summarized in Table 3 were obtained from the measurements.

TABLE 3

Initial concentration ($c_0$) and concentration at equilibrium ($c_{eq}$) of imines according to formula (I) in deuterium oxide

| | $c_0$ [mM] | $c_{eq}$ [mM] | $c_{eq}$ [%] | pD |
|---|---|---|---|---|
| Imine of formula (I) | | | | |
| Imine B | 10 | 4.11 | 41 | 10.4 |
| Imine A | 10 | 7.38 | 74 | 10.4 |
| Imine D | 10 | 2.9 | 29 | 9.3 |
| Imine D | 25 | 8.3 | 33 | 11.4 |
| Imine D | 50 | 23.1 | 46 | 11.5 |
| Imine D | 100 | 12 | 12 | 7.9 |
| Imine D | 100 | 47 | 47 | 11.7 |
| Imine D | 500 | 416 | 83 | 11.2 |
| Imine H | 10 | 4.7 | 47 | 10.9 |
| Imine E | 10 | 2.8 | 28 | 9.8 |
| Imine E | 25 | 8.8 | 35 | 11.0 |
| Imine E | 100 | 57.8 | 58 | 11.0 |
| Comparative imine | | | | |
| Imine C5 | 10 | 0 | 0 | 10.5 |
| Imine C6 | 10 | 1.5 | 15 | 11.1 |
| Imine C1 | 10 | 0 | 0 | 10.1 |
| Imine C1 | 100 | 6 | 6 | 10.1 |
| Imine C1 | 500 | 97 | 19 | 10.1 |

The data in Table 3 show that higher imine concentrations at the equilibrium were obtained with imines according to formula (I) than for the comparative imines. Imine C1 is mostly cleaved under the present conditions. This is because this imine is with a total HLB value of 19.30 very hydrophilic and can therefore not form organized aggregates under the given conditions. According to these results, imines of the present invention are more stable than comparative imines.

Example 6

Kinetics of Hydrolysis of Imines According to Formula (I) in Deuterium Oxide

Using the same experimental conditions as described in Example 5, the kinetics of the hydrolysis of imines according to formula (I) were compared to reference imines by $^1$H NMR spectroscopy. The data obtained is illustrated in Table 4.

TABLE 4

Initial rate of hydrolysis ($v_0$) and half-time of hydrolysis ($t_{1/2}$) of imines according to formula (I) in deuterium oxide at different initial concentrations ($c_0$)

| | $c_0$ [mM] | pD | $v_0$ [$10^{-3}$ mM/min] | $t_{1/2}$ [d] |
|---|---|---|---|---|
| Imine of formula (I) | | | | |
| Imine A | 10 | 10.1 | 1.3 | 2.48 |
| Imine B | 10 | 10.5 | 6.8 | 0.50 |
| Imine B | 25 | 10.6 | 9.7 | 0.90 |
| Imine B | 50 | 10.7 | 8.0 | 2.36 |
| Imine B | 100 | 11.1 | 9.3 | 3.60 |
| Imine B | 500 | 11.2 | 36.1 | 5.00 |
| Imine B | 10 | 10.7 | 6.3 | 0.52 |
| Imine B | 25 | 9.8 | 9.5 | 0.87 |
| Imine B | 100 | 9.4 | 9.9 | 3.26 |
| Comparative imine | | | | |
| Imine C5 | 10 | 10.5 | 14.8 | 0.19 |
| Imine C5 | 25 | 10.5 | 23.7 | 0.35 |
| Imine C5 | 100 | 10.4 | 856 | 0.22 |

The data in Table 4 show that the kinetics of hydrolysis of the imines according to formula (I) are slower than that of the comparative imine. Without being bound by theory, the increased stability of the imines according to formula (I) with respect to the comparative imine is believed to be the consequence of two phenomena: (a) the presence of the linker L in the imines according to formula (I) creates a hydrophobic environment around the imine link, thus preventing water from approaching, and ultimately leading to a local decrease of the concentration of water around the imine that shifts the equilibrium toward imine formation and (b) the presence of the hydrophobic linker decreases the critical micellar concentration (CMC) of the imine, and thus decreases the concentration of free easily-hydrolyzed imines in solution.

The half-time of hydrolysis of Imine C5 is around 5 h at all concentrations, which is consistent with pseudo-first order kinetics due to a very weak stabilization of the imine bond in the absence of the hydrophobic linker L. Imine B and Imine C according to formula (I) form more stable imines in solution due to the presence of a hydrophobic linker L between the hydrophilic part B and the hydrophobic part A. Their hydrolysis display an apparent linear relationship between the half-time of hydrolysis ($t_{1/2}$) and the initial concentration (co), a feature that is usually attributed to pseudo-zero order kinetics. This result has two implications: (a) it is possible to slow down the hydrolysis of the flavor or fragrance aldehyde or ketone by increasing the initial concentration of the imines of formula (I) (or, similarly, to increase the rate of hydrolysis of the imines upon dilution) and (b) it is possible to considerably increase the speed of hydrolysis by diluting the system.

Example 7

Hydrolysis of Imines According to Formula (I) in the Presence of Other Surfactants The influence of the presence of (co-)surfactants on the hydrolysis of imines according to formula (I) was investigated by $^1$H NMR spectroscopy in deuterium oxide (0.7 mL) as described in Example 5 with an initial imine concentration of 10 mM and 4 wt % of an additional surfactant. The following surfactants were tested: sodium dodecyl sulfate (SDS), sodium laureth sulphate (Texapon® NSO IS; trademark from BASF and commercially available from BASF), hexadecyl-trimethyl-ammonium bromide (cetrimonium bromide), 2,5,8,11,14,17,20,23,26,29,32,35,38,41,44,47,50,53, 56,59,62,65,68,71,74-pentacosaoxahexaheptacontan-76-yl stearate (PEG$_{25}$Monostearate), (polyethylene glycol)$_{9,10}$ 4-(1,1,3,3-tetramethylbutyl)-phenyl ether (Triton® X-100; trademark from Dow Chemical and commercially available from Sigma Aldrich), polyoxyethylene 20 sorbitan monooleate (Tween® 80; trademark from Uniquema, ICI Americas Inc. and commercially available from Sigma Aldrich). The data obtained from the measurements are summarized in Table 5.

TABLE 5

Initial concentration ($c_0$) and concentration at equilibrium ($c_{eq}$) of imines according to formula (I) in deuterium oxide in the presence of a co-surfactant

| Imine of formula (I) | Co-surfactant 4 wt % | $c_0$ [mM] | $c_{eq}$ [mM] | pD |
|---|---|---|---|---|
| Imine D | SDS | 10 | 8.93 | 10.5 |
| Imine D | Texapon ® NSO IS | 10 | 5.96 | 10.5 |
| Imine D | Certrimmonium bromide | 10 | 4.75 | 10.5 |
| Imine D | PEG$_{25}$Monostearate | 10 | 2.79 | 10.5 |
| Imine D | none | 10 | 2.95 | 10.5 |
| Imine E | PEG$_{25}$Monostearate | 10 | 7.50 | 10.4 |
| Imine E | PEG$_{25}$Monostearate | 10 | 6.40 | 4.4 *) |
| Imine E | none | 10 | 2.80 | 10.4 |

*) phosphate buffer (pD 4.4).

The data show that the presence of co-surfactants can increase (or keep at about equal level) the stability of the imines according to formula (I) in an aqueous environment. In the presence of PEG25Monostearate, a stabilization of the system was even observed under acidic conditions.

Example 8

Hydrolysis of Imines According to Formula (I) in Aqueous Surfactant Solution

To investigate the hydrolysis of the imines according to formula (I), a simple model formulation in deuterium oxide was prepared. Freeze-dried Texapon® NSO IS (trademark from BASF and commercially available from BASF) (4 wt %) was dissolved in deuterium oxide (95 wt %) at room temperature. The imine according to formula (I) (1 wt %) was added to the formulation at the beginning of the experiment (t=0), the pH was measured and the NMR measurements were started. The data are summarized in Table 6.

TABLE 6

Initial rate of hydrolysis ($v_0$) and half-time of hydrolysis ($t_{1/2}$) of imines according to formula (I) in a model formulation prepared with Texapon ® NSO IS

| | $c_0$ [mM] | pD | $v_0$ [$10^{-3}$ mM/min] | $t_{1/2}$ [h] |
|---|---|---|---|---|
| Imine of formula (I) | | | | |
| Imine A | 10 | 10.6 | n.d. | 9.2 |
| Imine B | 10 | 10.5 | 7.8 | 17.0 |
| Imine C | 10 | 10.5 | n.d. | 17.5 |
| Comparative imine | | | | |
| Imine C5 | 10 | 10.5 | 35.4 | 4.3 |

The imines according to formula (I) are considerably more stable than the comparative imine.

A second aqueous surfactant solution was prepared by dissolving freeze-dried sodium $C_{14-17}$ sec-alkyl sulphonate (Hostapur® SAS 60; trademark from Clariant GmbH and commercially available from Clariant GmbH; 7 wt %) and freeze-dried ethoxylated $C_{12-16}$ alcohols (Genapol® LA 70; trademark from Clariant GmbH and commercially available from Clariant GmbH; 17 wt %) in deuterium oxide (75 wt %) at room temperature. Then, sodium deuteroxide 40% in deuterium oxide was added until reaching a pH of 10. The imine according to formula (I) (1 wt %) was added to the formulation at the beginning of the experiment (t=0), the pH was measured and the NMR measurements were started. The data are summarized in Table 7.

TABLE 7

Initial rate of hydrolysis ($v_0$) and half-time of hydrolysis ($t_{1/2}$) of imines according to formula (I) in a model formulation prepared with Hostapur ® SAS 60 and Genapol ® LA 70

| Imine of formula (I) | $c_0$ [mM] | pD | $v_0$ [$10^{-3}$ mM/min] | $t_{1/2}$ (est.) [h] |
|---|---|---|---|---|
| Imine A | 10 | 10.4 | n.d. | 42.5 |
| Imine B | 10 | 12.0 | 2.2 | 41.0 |

Example 9

Solubilizing Capacity of Imines According to Formula (I)

TABLE 8

| Perfume composition | |
|---|---|
| Raw material | % |
| 2-Phenylethanol | 20 |
| Florol ® $^{1)}$ | 10 |
| Geraniol | 10 |
| Hedione ®$^{2)}$ | 10 |
| Benzyl acetate | 6 |
| Habanolide ®$^{3)}$ | 6 |
| Helvetolide ®$^{4)}$ | 4 |
| Citronellol | 2 |

TABLE 8-continued

Perfume composition

| Raw material | % |
|---|---|
| Dihydromyrcenol | 2 |
| Iso E Super ®[5] | 2 |
| Muscenone Delta[6] | 1 |
| Dipropylene glycol | 25 |

[1] tetrahydro-2-isobutyl-4-methyl-4(2H)-pyranol; origin: Firmenich SA, Geneva, Switzerland
[2] methyl dihydrojasmonate; origin: Firmenich SA, Geneva, Switzerland
[3] pentadecenolide; origin: Firmenich SA, Geneva, Switzerland
[4] (1S,1'R)-2-[1-(3',3'-dimethyl-1'-cyclohexyl)ethoxy]-2-methylpropyl propanoate; origin: Firmenich SA, Geneva, Switzerland
[5] 1-(octahydro-2,3,8,8-tetramethyl-2-naphthalenyl)-1-ethanone; origin: International Flavors & Fragrances, USA
[6] 3-methyl-5-cyclopentadecen-1-one; origin: Firmenich SA, Geneva, Switzerland Water (9.0 g) and the model perfume composition of Table 8 (0.3 g) are mixed under gentle agitation. The resulting solution is turbid. Imines of formula (I) are then added until a transparent solution was obtained. The minimal value of each surfactant necessary to obtain a transparent solution is listed in Table 9. The ratio fragrance to surfactant indicates the solubilizing capacity of the imines wherein higher ratio indicates higher solubilizing capacity of the imine.

TABLE 9

Solubilizing capacity of imines according to formula (I)

| | Water [%] | Fragrance [%] | Imine [%] | Fragrance/Surfactant Weight Ratio |
|---|---|---|---|---|
| Imine F | 89.11 | 2.97 | 7.92 | 2.7 |
| Imine G | 82.57 | 2.75 | 14.68 | 5.3 |
| Imine B | 91.65 | 3.05 | 5.30 | 1.7 |
| Imine C | 85.71 | 2.86 | 11.43 | 4.0 |
| Imine D | 82.87 | 2.76 | 14.36 | 5.2 |
| Imine E | 74.38 | 2.48 | 23.14 | 9.3 |

The imines according to formula (I) are thus useful to solubilize fragrances in an aqueous environment.

Example 10

Stability of Imines According to Formula (I) in Acidic Media

Compounds according to formula (I) were included into citral containing microemulsions formed by mixing a buffer solution at pH=2.6 (48% citric acid and 3.2% NaOH in water), Tween® 80 (trademark from Uniquema, ICI Americas Inc. and commercially available from Sigma Aldrich) and citral in the quantities listed in Table 10. A microemulsion without compounds according to formula (I) was prepared as a reference by mixing the buffer solution, Tween® 80 and citral in the proportions listed in Table 10. The two solutions contained equimolar amounts of citral.

TABLE 10

Composition of acidic formulations

| | Formulation 1 | | Formulation 2 | | Reference | |
|---|---|---|---|---|---|---|
| | [%] | [%] citral | [%] | [%] citral | [%] | [%] citral |
| Citral | 0.31 | 0.32 | 0.32 | 0.32 | 0.69 | 0.69 |
| Buffer 2.6 | 93.69 | | 91.78 | | 96.49 | |
| Imine D | 3.18 | 0.37 | — | — | — | — |
| Imine E | — | — | 5.09 | 0.37 | — | — |
| Tween ® 80 | 2.81 | | 2.82 | | 2.81 | |

At different time intervals the different formulations (0.305 g) were extracted by adding an aqueous solution of NaCl (15%, 2.745 g) and iso-octane (3.050 g). The mixtures were stirred (at 500 rpm for 10 min) and left equilibrating (5 min) to separate into two well distinguished phases. The phases were carefully separated and the organic phase (20 µL) analysed by GC/MS. GC/MS analyses were carried out on an Agilent 6890N Network GC system and an Agilent 5973 Network MS. Samples (1 µL) were eluted on an Agilent HP-5MS fused silica capillary column (30 m, inner diameter 250 µm, film thickness 0.25 µm) with a constant flow of helium (1 mL/min, corresponding to an average velocity of 37 cm/s). The injector temperature was at 250° C., the oven program starts at 80° C., a first ramp temperature at 10° C./min attains 200° C., followed by another one at 20° C./min to reach 260° C. This final temperature is held for 1 min. Citral was analyzed by single ion monitoring and the extracted citral concentrations were determined by external standard calibration.

The first extraction (t=0) was realized immediately after the preparation of the microemulsion. The microemulsion formulations were stored at 25° C. The degradation kinetics was followed during 20 d.

The citral degradation process can be expressed by Equation 2

$$C(t)=C(O)\exp(-kt) \qquad \text{Equation 2}$$

where $C(t)$ is the citral concentration at time t, $C(0)$ is the initial citral concentration (at t=0), k represents the rate of citral degradation. The citral concentration measured in the extraction experiments as a function of time (FIG. 1), were fitted with Equation 2. The degradation rates, as well as the initial maximum citral concentrations were determined. The time required to reach 50% of citral degradation is calculated with Equation 2 and listed in Table 11.

TABLE 11

Rates of citral degradation and time required to reach 50% of degradation

| Formulation | $C_0$ [mol/L] | k [d$^{-1}$] | t (50%) [d] |
|---|---|---|---|
| 1 | 157.43 | −0.063 | 17.40 |
| 2 | 126.27 | −0.036 | 23.13 |
| Reference | 103.06 | −0.055 | 13.47 |

The concentration of free citral in the reference sample is set as 100%. The citral content corresponding to the values exceeding 100% is generated by the hydrolysis of imines of formula (I).

The data demonstrate that the formulations containing an imine according to formula (I) significantly decrease the degradation kinetics of the flavor or fragrance molecule as compared to a reference formulation without compound of formula (I). Imine E is the more efficient molecule decreasing the degradation rate 1.53 times. As it can be seen from the curves the degradation process depends on the initial citral concentration.

Example 11

Solubilizing Capacity and Controlled Release Properties of Imines According to Formula (I)

A model perfume with the composition listed in Table 8 (Example 9) was prepared. Then water and the model perfume were mixed and either an imine of formula (I) or a commercial surfactant ($PEG_{25}$Monostearate, serving as the reference) was added to give the formulations indicated in Table 12. Homogenous microemulsions were obtained for Formulations 1, 2 and the Reference, thus showing the capability of these molecules to act as a surfactant and to solubilize the perfume. Attempts to dissolve the model perfume with an equivalent amount of Imine C1 failed. Instead of a homogenous system, perfume droplets were formed. Imine C1 is thus not capable to solubilize the perfume and does not act as a surfactant.

TABLE 12

Composition of formulations

| | Formulation 1 [%] | Formulation 2 [%] | Reference [%] |
|---|---|---|---|
| Model perfume | 2.97 | 2.97 | 2.94 |
| Water | 89.11 | 89.11 | 88.24 |
| Imine B | 7.92 | — | — |
| Imine F | — | 7.92 | — |
| $PEG_{25}$Monostearate | — | — | 8.82 |

The different formulations and the reference (25 µL) were each pipetted onto a watch glass (4 cm) and placed inside a headspace sampling cell (ca. 625 mL inner volume). A constant flow of air (ca. 200 mL/min, filtered through activated charcoal and aspirated through a saturated solution of NaCl to ensure a constant humidity of the air of ca. 75%) was pumped through the headspace cell. The volatiles evaporating from the watch glass were alternatingly adsorbed onto a waste Tenax® cartridge (w), then onto a clean Tenax® cartridge (c), according to the following time sequence: 15 min (w), 3 min (c), 17 min (w), 3 min (c), 12 min (w), 8 min (c), 19 min (w), 8 min (c), 53 min (w), 10 min (c), 50 min (w) and 10 min (c), to result in a total sampling time of 208 min after the last sampling. The waste cartridges were discarded; the clean cartridges were thermally desorbed on a PerkinElmer TurboMatrix 350 thermodesorber, coupled to an Agilent 7890A gas chromatograph and connected to an Agilent 5975C mass spectrometer (MS). The volatiles were eluted on a HP-1 capillary column (30 m×0.250 mm, film 0.25 µm) with a temperature gradient starting at 100° C. for 2 min, then moving at 5° C./min to 220° C. (26 min) and analyzed by MS using single ion monitoring with time window programming. Quantification was carried out by external standard calibration using reference solutions in ethanol at different concentrations, which were directly injected onto clean Tenax® cartridges and processed under the same conditions. Because of the large differences in concentrations, calibrations were carried out in two groups. All measurements were carried out at least in duplicate.

The headspace data recorded for the evaporation of the different fragrance ingredients in the model perfume are summarized in FIG. 4.

The data show that the imines according to formula (I) have a similar impact on the evaporation of the perfume ingredients as the reference surfactant, thus showing that they act as a surfactant. Additionally, they are capable to release an additional fragrance molecule (hexylcinnamic aldehyde in the case of Imine B and (Z)-4-dodecenal in the case of Imine F) in a controlled manner by cleavage of the surfactant structure.

Example 12

Solubilizing Capacity and Controlled Release Properties of Imines According to Formula (I) as a Mixture with a Second Surfactant A model perfume with the composition listed in Table 8 (Example 9) was prepared. Then water and the model perfume were mixed, and a mixture of an imine of formula (I) and a commercial surfactant ($PEGs_{25}$Monostearate) (ca. 1:1 molar ratio) was added to give the formulations indicated in Table 13. Homogenous microemulsions were obtained.

TABLE 13

Composition of formulations

| | Formulation 1 [%] | Formulation 2 [%] | Reference (see Example 11) [%] |
|---|---|---|---|
| Model perfume | 3.00 | 3.00 | 2.94 |
| Water | 88.80 | 89.00 | 88.24 |
| Imine B | 3.88 | — | — |
| Imine F | — | 3.74 | — |
| $PEG_{25}$Monostearate | 4.34 | 4.28 | 8.82 |

The different formulations (25 µL) were each pipetted onto a watch glass (4 cm), placed inside a headspace sampling cell (ca. 625 mL inner volume) and analyzed as described in Example 11. The volatiles evaporating from the watch glass were alternatingly adsorbed onto a waste Tenax® cartridge (w), then onto a clean Tenax® cartridge (c), according to the following time sequence: 15 min (w), 3 min (c), 17 min (w), 3 min (c), 17 min (w), 3 min (c), 17 min (w), 5 min (c), 55 min (w), 8 min (c), 52 min (w), 8 min (c), 52 min (w) and 10 min (c), 50 min (w), 10 min (c), 50 min (w), 10 min (c), to result in a total sampling time of 385 min after the last sampling. All measurements were carried out at least in duplicate.

The headspace data recorded for the evaporation of the different fragrance ingredients in the model perfume are summarized in FIG. 5.

The data recorded for the headspace analysis showed that Formulations 1 and 2 containing an imine according to formula (I) together with a commercial surfactant released the corresponding fragrance molecule (hexylcinnamic aldehyde in the case of Imine B and (Z)-4-dodecenal in the case of Imine F) by cleavage of the surfactant structure. At the same time, with respect to the reference sample without an imine according to formula (I), a higher amount of fragrance evaporated at the beginning of the measurements, before reaching similar headspace concentrations as the reference at the end of the experiment. It is thus advantageous to combine an imine according to formula (I) with other surfactants.

Example 13

Controlled Release Properties of Imines According to Formula (I) in a Model Shower Gel Application Two model shower gel formulations with the compositions listed in Table 14 were prepared.

TABLE 14

Composition of model shower gels

| | Shower Gel 1 (non-structured) [%] | Shower Gel 2 (structured) [%] |
|---|---|---|
| Water | 61.20 | 49.25 |
| EDTA B powder[1] | 0.10 | 0.05 |
| Carbopol ® Aqua SF-1[2] | — | 6.00 |
| Zetesol AO 328 U[3] | 27.00 | 35.00 |
| Sodium hydroxide 20% | — | 1.00 |
| Tego ® Betain F 50[4] | 8.00 | 8.00 |
| Kathon ® SG[5] | — | 0.10 |
| Citric acid (40%) | 1.00 | 0.50 |
| Sodium benzoate | 0.50 | — |
| 1,2 propylene glycol | 2.00 | — |
| Merquat ® 550[6] | 0.20 | — |

[1] Tetrasodium EDTA; trademark and origin: BASF
[2] Acrylates Copolymer; trademark and origin: NOVEON
[3] Sodium C12-C15 Pareth Sulfate; trademark and origin: ZSCHIMMER & SCHWARZ
[4] Cocamidopropyl Betaine; trademark and origin: GOLDSCHMIDT
[5] Methylchloroisothiazolinone and Methylisothiazolinone; trademark and origin: ROHM & HASS
[6] Polyquaternium-7;; trademark and origin: LUBRIZOL With mechanical stirring, Imine F (0.5%) was added to each of the model shower gel formulations (99.5%) listed in Table 14. Both formulations containing Imine F (ca. 27 mg) were pipetted onto a watch glass (4 cm) and placed inside a headspace sampling cell (ca. 625 mL inner volume), respectively. A constant flow of air (ca. 200 mL/min, filtered through activated charcoal and aspirated through a saturated solution of NaCl to ensure a constant humidity of the air of ca. 75%) was pumped through the headspace cell. The volatiles evaporating from the watch glass were alternatingly adsorbed onto a waste Tenax® cartridge (w), then onto a clean Tenax® cartridge (c), according to the following time sequence: 15 min (w), 3 min (c), 17 min (w), 3 min (c), 17 min (w), 3 min (c), 17 min (w), 5 min (c), 55 min (w), 8 min (c), 52 min (w) and 8 min (c), 52 min (w) and 10 min (c) to result in a total sampling time of 265 min after the last sampling. The waste cartridges were discarded; the clean cartridges were thermally desorbed on a PerkinElmer TurboMatrix 350 thermodesorber, coupled to an Agilent 7890A gas chromatograph and connected to an Agilent 5975C mass spectrometer (MS). The volatiles were eluted on a HP-1 capillary column (30 m×0.250 mm, film 0.25 μm) with a temperature gradient starting at 100° C. for 2 min, then moving at 5° C./min to 220° C. (26 min) and analyzed by MS using single ion monitoring with time window programming. Quantification was carried out by external standard calibration using reference solutions in ethanol at different concentrations, which were directly injected onto clean Tenax® cartridges and processed under the same conditions. All measurements were carried out at least in duplicate.

In a second measurement, both formulations containing Imine F (ca. 27 mg) were pipetted onto a watch glass (4 cm) and placed inside a headspace sampling cell (ca. 625 mL inner volume), respectively. Then water (750 μL) was added to simulate the dilution of the samples occurring during the use of a shower gel. The samples were then analyzed as described above.

The results obtained from these measurements are summarized in Table 15.

TABLE 15

Dynamic headspace concentrations of (Z)-4-dodecenal released from Imine F in different shower gel formulations with and without dilution.

| | Headspace concentrations of (Z)-4-dodecenal [ng/L] measured for | | | |
|---|---|---|---|---|
| Sampling time | Shower Gel 1 (non-structured) | | Shower Gel 2 (structured) | |
| [min] | undiluted | diluted | undiluted | diluted |
| 18 | 3.0 | 17.2 | 1.2 | 8.8 |
| 38 | 3.1 | 12.9 | 0.9 | 6.7 |
| 58 | 2.8 | 11.1 | 0.8 | 4.4 |
| 80 | 3.4 | 13.2 | 0.7 | 6.4 |
| 143 | 4.1 | 7.9 | 0.4 | 6.0 |
| 203 | 1.1 | 6.9 | 0.6 | 5.5 |
| 265 | 1.1 | 4.7 | 0.3 | 5.1 |

The headspace data show that the cleavable surfactant only released small amounts of (Z)-4-dodecenal when integrated into the concentrated shower gel formulation. Dilution of the sample triggered the release of the aldehyde by cleaving the surfactant, and larger amounts of (Z)-4-dodecenal were released. In the case of Shower Gel 1, dilution increased the headspace concentrations by a factor of ca. 2 to 6, in the case of Shower Gel 2, dilution increased the headspace concentrations even more, namely by a factor of ca. 6 to 17. Cleavable surfactants according to formula (I) are thus suitable for use in applications where dilution occurs, such as in a shower gel.

What is claimed is:

1. A compound of formula

(I)

having a total hydrophilic-lipophilic balance comprised between 3 and 18 being calculated using the Effective Chain Length model and wherein A is a group capable of releasing a flavor or fragrance aldehyde of formula $(R^1)$CHO or a flavor or fragrance ketone of formula $(R^1)(R^2)$CO and is of formula

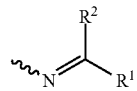

(II)

wherein the wavy line indicates the location of the bond between L and A; $R^1$ and $R^2$ represent independently from each other a hydrogen atom or a linear saturated or unsaturated $C_1$-$C_{18}$ hydrocarbon group, optionally substituted with one to three oxygen atoms in the form of a hydroxyl, carbonyl, ether or ester group, or a branched or cyclic, saturated or unsaturated $C_3$-$C_{18}$ hydrocarbon group, optionally substituted with one to three oxygen atoms in the form of a hydroxyl, carbonyl, ether or ester group or $R^1$ and $R^2$, when taken together, represent a $C_{4-18}$ linear, branched or cyclic alkanediyl group, optionally substituted with one to three oxygen atoms in the form of a hydroxyl, carbonyl, ether or ester group, provided that at least one of the $R^1$ or $R^2$ groups has 6 consecutive carbon atoms and that both $R^1$ and $R^2$ taken together comprise a maximum of 18 carbon atoms;

L is a $OC_6H_4CR^3{}_2CR^3{}_2$ group or a $(OCH_2CHR^3)_q$ group, wherein $R^3$ represents a hydrogen atom or a methyl group and q is an integer varying between 3 and 10; and Q is a polyimine, a poly(ethylene oxide), a poly(propylene oxide), a polypeptide, or a polysaccharide.

2. The compound according to claim 1, wherein Q represents a poly(ethylene oxide), a poly(propylene oxide), or a polypeptide.

3. The compound according to claim 1, wherein Q represents a $CH_3(OC_2H_4)_m$ group wherein m is an integer varying between 11 and 30.

4. A solubilizing system comprising water, perfuming or flavoring oil and at least one compound of formula (I) as defined in claim 3.

5. The solubilizing system according to claim 4, wherein the solubilizing system comprises water and dispersed perfuming or flavoring ingredient-containing oil droplets which are stabilized by the at least one compound of formula (I).

6. The solubilizing system according to claim 5, characterized in that the perfuming or flavoring ingredient-containing oil comprises perfuming or flavoring ingredients being an aldehyde of formula $R^1CH(O)$ or a ketone of formula $(R^1)(R^2)C(=O)$ wherein $R^1$ and $R^2$ represent independently from each other a hydrogen atom or a linear saturated or unsaturated $C_1$-$C_{18}$ hydrocarbon group, optionally substituted with one to three oxygen atoms in the form of a hydroxyl, carbonyl, ether or ester group, or a branched or cyclic, saturated or unsaturated $C_3$-$C_{18}$ hydrocarbon group, optionally substituted with one to three oxygen atoms in the form of a hydroxyl, carbonyl, ether or ester group or $R^1$ and $R^2$, when taken together, represent a $C_{4-18}$ linear, branched or cyclic alkanediyl group, optionally substituted with one to three oxygen atoms in the form of a hydroxyl, carbonyl, ether or ester group, provided that at least one of the $R^1$ or $R^2$ groups has 6 consecutive carbon atoms and that both $R^1$ and $R^2$ taken together comprise a maximum of 18 carbon atoms.

7. A perfuming or flavoring composition comprising:
a) as perfuming or flavoring ingredient, at least one compound of formula (I) as defined in claim 1;
b) at least one ingredient selected from the group consisting of a perfumery or flavor carrier, a perfuming or flavoring co-ingredient and mixtures thereof; and
c) optionally at least one perfumery or flavor adjuvant.

8. A perfuming or flavoring consumer product comprising at least one compound of formula (I) as defined in claim 1.

9. The perfuming consumer product according to claim 8, wherein the consumer product is a perfuming consumer product comprising a perfume, a fabric care product, a body-care product, a cosmetic preparation, a skin-care product, an air care product or a home care product or the consumer product is a flavoring consumer product comprising a beverage.

10. The perfuming consumer product according to claim 9, wherein the perfumery consumer product is selected from the group consisting of a fine perfume, a splash or eau de perfume, a cologne, a shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, and a car care product.

11. A method for releasing active volatile aldehydes or ketones comprising applying to a composition, an article or a surface an effective amount of at least one compound of formula (I) as defined in claim 1.

12. A method for solubilizing and/or stabilizing hydrophobic molecules in an aqueous environment comprising adding to said aqueous environment an effective amount of at least one compound of formula (I) as defined in claim 1.

13. A perfuming or flavoring composition comprising:
a) as perfuming or flavoring ingredient, a solubilizing system as defined in claim 4;
b) at least one ingredient selected from the group consisting of a perfumery or flavor carrier, a perfuming or flavoring co-ingredient and mixtures thereof; and
c) optionally at least one perfumery or flavor adjuvant.

14. A perfuming or flavoring consumer product comprising a solubilizing system, as defined in claim 4.

15. The perfuming consumer product according to claim 14, wherein the consumer product is a perfuming consumer product comprising a perfume, a fabric care product, a body-care product, a cosmetic preparation, a skin-care product, an air care product or a home care product or the consumer product is a flavoring consumer product comprising a beverage.

16. The perfuming consumer product according to claim 15, wherein the perfumery consumer product is selected from the group consisting of a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, and a car care product.

17. A method for releasing active volatile aldehydes or ketones comprising applying to a composition, an article or a surface an effective amount of the solubilizing system of claim 6.

18. The compound according to claim 1, wherein L represents a $OC_6H_4CH_2CH_2$ group or a $(OCH_2CH(CH_3))_q$ group wherein q is an integer varying between 3 and 10.

* * * * *

UNITED STATES PATENT AND TRADEMARK OFFICE
CERTIFICATE OF CORRECTION

| | | |
|---|---|---|
| PATENT NO. | : 11,344,493 B2 | Page 1 of 1 |
| APPLICATION NO. | : 16/342523 | |
| DATED | : May 31, 2022 | |
| INVENTOR(S) | : Eric Lutz et al. | |

It is certified that error appears in the above-identified patent and that said Letters Patent is hereby corrected as shown below:

On the Title Page

In item (73), in Assignees, delete "FIRMENICH SA" and insert therefor -- FIRMENICH SA and CNRS - CENTRE NATIONAL DE LA RECHERCHE SCIENTIFIQUE --.

Signed and Sealed this
Fifth Day of December, 2023

Katherine Kelly Vidal
*Director of the United States Patent and Trademark Office*